(12) United States Patent
Mitchell et al.

(10) Patent No.: US 11,904,016 B2
(45) Date of Patent: Feb. 20, 2024

(54) HEMATOPOIETIC STEM CELLS IN COMBINATORIAL THERAPY WITH IMMUNE CHECKPOINT INHIBITORS AGAINST CANCER

(71) Applicant: University of Florida Research Foundation, Incorporated, Gainesville, FL (US)

(72) Inventors: Duane Mitchell, Gainesville, FL (US); Catherine Flores, Gainesville, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 752 days.

(21) Appl. No.: 16/847,484

(22) Filed: Apr. 13, 2020

(65) Prior Publication Data

US 2021/0008200 A1    Jan. 14, 2021

Related U.S. Application Data

(63) Continuation of application No. 15/748,284, filed as application No. PCT/US2016/044718 on Jul. 29, 2016, now Pat. No. 10,660,954.

(60) Provisional application No. 62/296,826, filed on Feb. 18, 2016, provisional application No. 62/296,849, filed on Feb. 18, 2016, provisional application No. 62/296,866, filed on Feb. 18, 2016, provisional application No. 62/199,916, filed on Jul. 31, 2015.

(51) Int. Cl.
| | |
|---|---|
| *A61K 39/395* | (2006.01) |
| *A61K 35/28* | (2015.01) |
| *A61P 35/00* | (2006.01) |
| *C07K 16/28* | (2006.01) |
| *C12N 5/00* | (2006.01) |
| *A61P 31/12* | (2006.01) |
| *A61K 45/06* | (2006.01) |
| *A61K 39/00* | (2006.01) |

(52) U.S. Cl.
CPC .......... *A61K 39/3955* (2013.01); *A61K 35/28* (2013.01); *A61K 45/06* (2013.01); *A61P 31/12* (2018.01); *A61P 35/00* (2018.01); *C07K 16/28* (2013.01); *C07K 16/2818* (2013.01); *C12N 5/00* (2013.01); *A61K 2039/5154* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 5,811,097 A | 9/1998 | Allison et al. | |
| 5,855,887 A | 1/1999 | Allison et al. | |
| 6,051,227 A | 4/2000 | Allison et al. | |
| 6,984,720 B1 | 1/2006 | Korman et al. | |
| 7,034,121 B2 | 4/2006 | Carreno et al. | |
| 7,960,434 B2 | 6/2011 | Turkson et al. | |
| 8,168,179 B2 | 5/2012 | Honjo et al. | |
| 8,236,304 B2 | 8/2012 | Noelle et al. | |
| 8,318,916 B2 | 11/2012 | Korman et al. | |
| 8,475,790 B2 | 7/2013 | Kunkel | |
| 10,660,954 B2 | 5/2020 | Mitchell et al. | |
| 2002/0039581 A1 | 4/2002 | Carreno et al. | |
| 2002/0086014 A1 | 7/2002 | Korman et al. | |
| 2005/0201994 A1 | 9/2005 | Korman et al. | |
| 2011/0020274 A1 | 1/2011 | Zheng et al. | |
| 2011/0271358 A1 | 11/2011 | Freeman et al. | |
| 2012/0251537 A1 | 10/2012 | Ahmed et al. | |
| 2013/0017199 A1 | 1/2013 | Langermann | |
| 2013/0108651 A1 | 5/2013 | Carven et al. | |
| 2013/0109843 A1 | 5/2013 | Carven et al. | |
| 2013/0177557 A1 | 7/2013 | Noelle et al. | |
| 2013/0230514 A1 | 9/2013 | Langermann et al. | |
| 2013/0237580 A1 | 9/2013 | Sasikumar et al. | |
| 2013/0280265 A1 | 10/2013 | Rolland et al. | |
| 2013/0309250 A1 | 11/2013 | Cosgwell et al. | |
| 2014/0056892 A1 | 2/2014 | Noelle et al. | |
| 2014/0105912 A1 | 4/2014 | Noelle et al. | |
| 2014/0220012 A1 | 8/2014 | Noelle et al. | |
| 2014/0341920 A1 | 11/2014 | Noelle et al. | |
| 2015/0320859 A1 | 11/2015 | Maecker et al. | |
| 2016/0222121 A1 | 8/2016 | Johnson et al. | |

FOREIGN PATENT DOCUMENTS

| | | |
|---|---|---|
| CN | 105246507 A | 1/2016 |
| EP | 1212422 B1 | 2/2007 |
| EP | 2552947 A2 | 2/2013 |
| EP | 2170959 B1 | 10/2013 |
| WO | WO 2001/014424 A2 | 3/2001 |
| WO | WO 2004/035607 A2 | 4/2004 |
| WO | WO 2010/039997 A2 | 4/2010 |
| WO | WO 2011/120013 A2 | 9/2011 |
| WO | WO 2014/039983 A1 | 3/2014 |
| WO | WO 2015/048312 A1 | 4/2015 |
| WO | WO 2015/097536 A2 | 7/2015 |
| WO | WO 2015/191881 A2 | 12/2015 |

OTHER PUBLICATIONS

International Search Report and Written Opinion for PCT/US2016/044718, dated Dec. 8, 2016.
International Preliminary Report on Patentability for PCT/US2016/044718, dated Feb. 15, 2018.
Partial Supplementary European Search Report dated Mar. 26, 2019, in connection with EP Application No. 16833610.5.
Extended European Search Report dated Jul. 10, 2019, in connection with EP Application No. 16833610.5.
Brahmer et al., Safety and activity of anti-PD-L1 antibody in patients with advanced cancer. N Engl J Med. Jun. 28, 2012;366(26):2455-65. doi: 10.1056/NEJMoa1200694. Epub Jun. 2, 2012.

(Continued)

*Primary Examiner* — Daniel C Gamett
(74) *Attorney, Agent, or Firm* — Wolf, Greenfield & Sacks, P.C.

(57) ABSTRACT

The novel synergistic combination of immune checkpoint blockade and hematopoietic stem cell transplantation and/or hematopoietic stem cell mobilization yield synergistic effects in disease therapy.

22 Claims, 15 Drawing Sheets

(56) References Cited

OTHER PUBLICATIONS

Camacho et al., Phase 1 clinical trial of anti-CTLA4 human monoclonal antibody CP-675,206 in patients (pts) with advanced solid malignancies. J. Clin. Ocology 2004;22(145):Abstract No. 2505.

Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80. doi: 10.1073/pnas.0915174107. Epub Feb. 16, 2010.

Dolan et al., PD-1 pathway inhibitors: changing the landscape of cancer immunotherapy. Cancer Control. Jul. 2014;21(3):231-7.

Herbst et al., Predictive correlates of response to the anti-PD-L1 antibody MPDL3280A in cancer patients. Nature. Nov. 27, 2014;515(7528):563-7. doi: 10.1038/nature14011.

Hurwitz et al., CTLA-4 blockade synergizes with tumor-derived granulocyte-macrophage colony-stimulating factor for treatment of an experimental mammary carcinoma. Proc Natl Acad Sci U S A. Aug. 18, 1998;95(17):10067-71.

Ishida et al., Induced expression of PD-1, a novel member of the immunoglobulin gene superfamily, upon programmed cell death. Embo J. Nov. 1992;11(11):3887-95.

Kondo et al., SATB1 Plays a Critical Role in Establishment of Immune Tolerance. J Immunol Dec. 14, 2015, 1501429; DOI: https://doi.org/10.4049/jimmunol.1501429.

Latchman et al., PD-L2 is a second ligand for PD-1 and inhibits T cell activation. Nat Immunol. Mar. 2001;2(3):261-8.

Leong et al., Isolation of purified autologous peripheral blood CD34+ cells with low T cell content using CliniMACS device—a local experience. Malays J Pathol. Jun. 2008;30(1):31-6.

Lines et al., VISTA is an immune checkpoint molecule for human T cells. Cancer Res. Apr. 1, 2014;74(7):1924-32. doi: 10.1158/0008-5472.CAN-13-1504.

Lipson et al., Ipilimumab: an anti-CTLA-4 antibody for metastatic melanoma. Clin Cancer Res. Nov. 15, 2011;17(22):6958-62. doi: 10.1158/1078-0432.CCR-11-1595. Epub Sep. 7, 2011.

Liu et al., 2B4 (CD244) induced by selective CD28 blockade functionally regulates allograft-specific CD8+ T cell responses. J Exp Med. Feb. 10, 2014;211(2):297-311. doi: 10.1084/jem.20130902. Epub Feb. 3, 2014.

Liu et al., Immune-checkpoint proteins VISTA and PD-1 nonredundantly regulate murine T-cell responses. Proc Natl Acad Sci U S A. May 26, 2015;112(21):6682-7. doi: 10.1073/pnas.1420370112. Epub May 11, 2015.

Mokyr et al., Realization of the therapeutic potential of CTLA-4 blockade in low-dose chemotherapy-treated tumor-bearing mice. Cancer Res. Dec. 1, 1998;58(23):5301-4.

Rozali et al., Programmed Death Ligand 2 in Cancer-Induced Immune Suppression. Clinical and Developmental Immunology. 2012;2012:656340, 8 pages. http://dx.doi.org/10.1155/2012/656340.

Shinohara et al., Structure and chromosomal localization of the human PD-1 gene (PDCD1). Genomics. Oct. 1994;23(3):704-6.

Stewart et al., Identification and Characterization of MEDI4736, an Antagonistic Anti-PD-L1 Monoclonal Antibody. Cancer Immunol Res. Sep. 2015;3(9):1052-62. doi: 10.1158/2326-6066.CIR-14-0191. Epub May 5, 2015.

Topalian et al., Safety, activity, and immune correlates of anti-PD-1 antibody in cancer. N Engl J Med. Jun. 28, 2012;366(26):2443-54. doi: 10.1056/NEJMoa1200690. Epub Jun. 2, 2012.

Vanneman et al., Combining immunotherapy and targeted therapies in cancer treatment. Nat Rev Cancer. Mar. 22, 2012;12(4):237-51. doi: 10.1038/nrc3237. Review.

Wang et al., VISTA, a novel mouse Ig superfamily ligand that negatively regulates T cell responses. J Exp Med. Mar. 14, 2011;208(3):577-92. doi: 10.1084/jem.20100619. Epub Mar. 7, 2011.

Yue et al., Targeting STAT3 in cancer: how successful are we? Expert Opin Investig Drugs. Jan. 2009;18(1):45-56. doi: 10.1517/13543780802565.

Armand et al., An Anti-Pd-1 Antibody Is Effective In Diffuse Large B-Cell Lymphoma. Cancer Discov. Dec. 2013; 3(12):1327.

Armand et al., Disabling immune tolerance by programmed death-1 blockade with pidilizumab after autologous hematopoietic stem-cell transplantation for diffuse large B-cell lymphoma: results of an international phase II trial. J Clin Oncol. Nov. 20, 2013;31(33):4199-206. doi: 10.1200/JCO.2012.48.3685. Epub Oct. 14, 2013.

Dutta et al., Myocardial Infarction Activates CCR2+ Hematopoietic Stem and progenitor Cells. Cell Stem Cell. May 7, 2015; 16(5):477-87. doi: 10.1016/j.stem.2015.04.008.

Remberger et al., Effect of Total Nucleated and CD34(+) Cell Dose on Outcome after Allogeneic Hematopoietic Stem Cell Transplantation. Biol Blood Marrow Transplant. May 2015;21(5):889-93. doi: 10.1016/j.bbmt.2015.01.025. Epub Feb. 4, 2015.

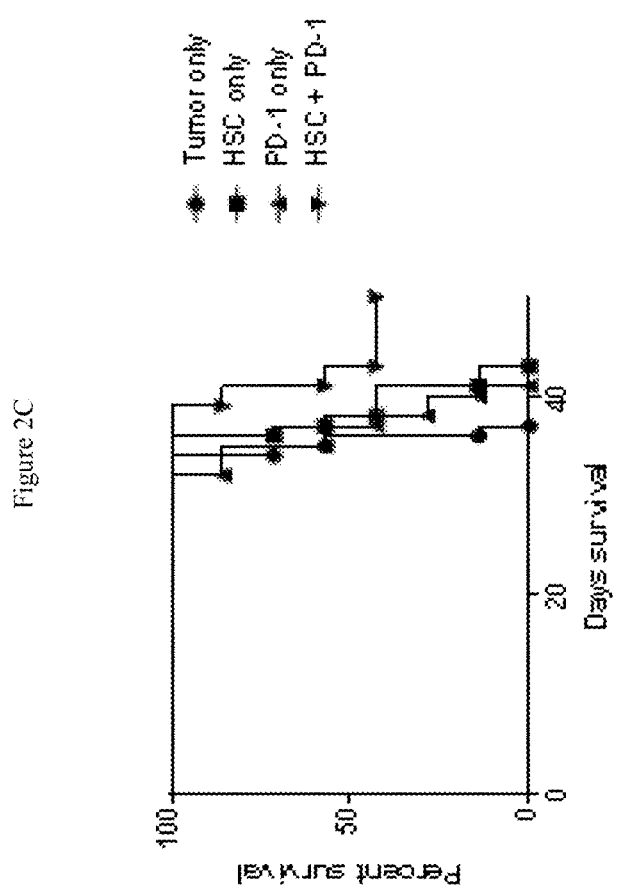

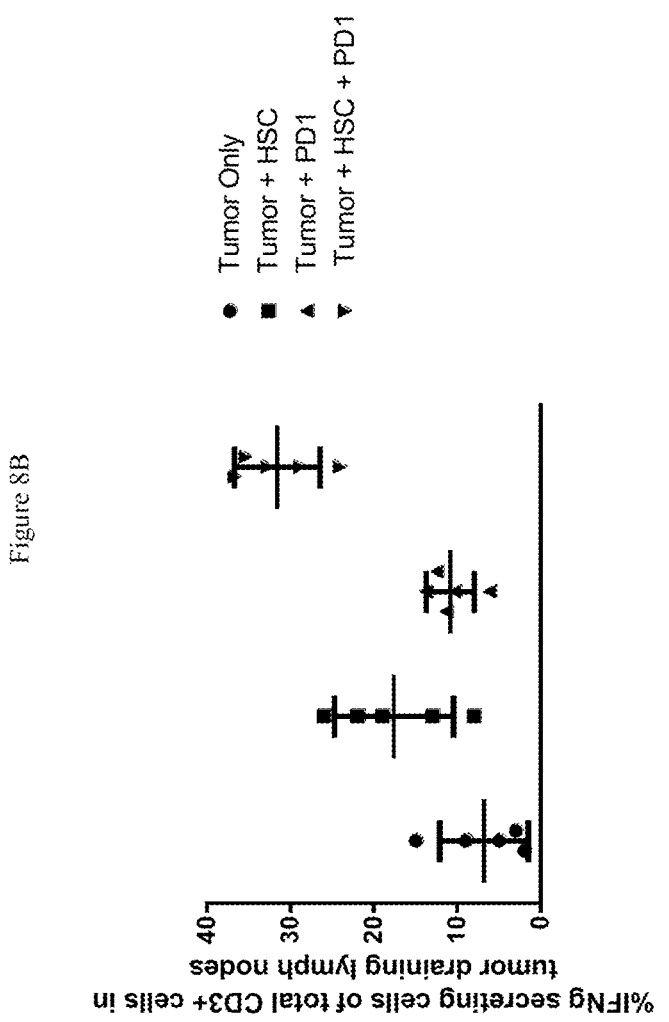

HEMATOPOIETIC STEM CELLS IN COMBINATORIAL THERAPY WITH IMMUNE CHECKPOINT INHIBITORS AGAINST CANCER

RELATED APPLICATIONS

This application is a continuation of U.S. application Ser. No. 15/748,284, filed Jan. 29, 2018, which is a national stage filing under 35 U.S.C. § 371 of international application number PCT/US2016/044718, filed Jul. 29, 2016, which was published under PCT Article 21(2) in English and claims the benefit under 35 U.S.C. § 119(e) of U.S. provisional application serial number 62/199,916, filed Jul. 31, 2015, U.S. provisional application number 62/296,826, filed Feb. 18, 2016, U.S. provisional application number 62/296,849, filed Feb. 18, 2016, and U.S. provisional application number 62/296,866, filed Feb. 18, 2016, the contents of all of which are incorporated herein by reference in their entireties.

BACKGROUND OF THE DISCLOSURE

The use of immune checkpoint inhibitors that bind immune checkpoint molecules such as programmed death 1 (PD-1), programmed death ligand-1 (PD-L1), cytotoxic T-lymphocyte-associated antigen (CTLA-4), or V-domain Ig suppressor of T cell activation (VISTA) and cause immune checkpoint blockade is a promising approach being investigated for the treatment of cancer and infectious diseases. Despite impressive therapeutic responses in clinical trials in a large number of cancers, not all subjects with those cancers respond to immune checkpoint blockade. In addition, there are many cancers for which a therapeutic response to treatment with antibodies that bind immune checkpoint molecules (e.g., PD-1 or CTLA-4) has not been evident.

Enhancing CD4 and CD8 T cell activity against a variety of cells, including cancer cells, is another approach being investigated to treat cancers and infectious diseases. In one strategy, T lymphocytes are stimulated with antigen, expanded ex-vivo, and then transfused into a subject. This is a form of adoptive cellular therapy (ACT). Certain ACT strategies have been shown in early stage clinical trials to induce cancer regression. ACT may be particularly useful in treating cancers and/or infectious diseases that arise following immune-ablation and hematopoietic stem cell transplantation (HSCT).

Still another approach being investigated for treating cancer is hematopoietic stem cell transplantation (HSCT) and/or hematopoietic stem cell (HSC) mobilization. HSCT and/or HSC mobilization, when combined with treatments to induce mild lymphopenia, may enhance the effects of certain cell based immunotherapies.

Immune checkpoint blockade alone, e.g., anti-PD1, anti-PD-L1, anti-CTLA-4, or anti-VISTA mediated blockade, and the administration of HSCs or an HSC mobilizing agent alone, do not show clinical effects in many subjects with different cancers. However, it has been discovered according to the present disclosure that the combination of HSC transfer with immune checkpoint blockade (e.g., anti-PD-1 mediated blockade or anti-VISTA mediated blockade), is synergistic in the treatment of cancer. This synergy allows for the treatment of a cancer that is refractory to immune checkpoint blockade by treatment with an immune checkpoint inhibitor and HSC transplantation, and can result in significant long-term regression of a checkpoint inhibitor-resistant cancer. The discovery of the present disclosure that combination treatment with an anti-PD-1 antibody and hematopoietic stem cell transplantation reverses resistance to immune checkpoint blockade using anti-PD-1 antibody monotherapy was verified in multiple brain tumor models (e.g., brain stem glioma, cortical glioblastoma, and medulloblastoma).

SUMMARY OF THE DISCLOSURE

The inventors have made the unique observation that bone marrow derived-hematopoietic stem cells (HSCs) administered to experimental tumor-bearing mice promote the persistence and survival of activated interferon gamma (IFNγ) secreting T cells within the tumor microenvironment and tumor-draining lymph nodes in mice receiving immune checkpoint blockade with an immune checkpoint inhibitor.

Immune checkpoint blockade using anti-PD-1, anti-PD-L1, or anti-CTLA-4 monoclonal antibodies has been shown to be an important and effective modality in many cancers (melanoma, non-small cell lung cancer, etc.) and is currently being evaluated for efficacy against a number of human tumors and for potential as a tumor predictive biomarker (Mahoney et al., 2015; Shih et al., 2014; Dolan et al., 2014, incorporated by reference herein, in their entireties).

Immune checkpoint blockade using anti-VISTA monoclonal antibodies has been shown in murine tumor models, to elevate $CD8^+$ T cell activation assessed by CD25, IFN-γ and TNF-α expression, but not clearly affect tumor growth (Kondo et al. 2015. J. of Immun. V194). VISTA induces immunosuppressive activities on T cells both in vitro and in vivo and VISTA blockade enhances T cell-mediated immunity in an autoimmune disease model (Wang et al. 2011. JEM 208(3):577-92). VISTA blockade, in combination with other immunotherapy strategies, e.g., HSCT or HSC mobilization, may be an important mediator in controlling the development of autoimmunity and immune responses to cancers.

Despite impressive clinical responses in a large number of cancers, responses to treatment with immune checkpoint inhibitors (e.g., anti-immune checkpoint antibodies) are currently observed in only a subset of treated patients. Results disclosed herein indicate that the combination treatment with HSC transfer and immune checkpoint inhibitors, e.g., anti-PD-1, anti-PD-L1, anti-CTLA-4, or anti-VISTA antibodies, is synergistic in treating tumors that are resistant to the anti-immune checkpoint antibodies alone, wherein the combination is curative in a significant fraction of treated animals. The combination of HSCT and treatment with an immune checkpoint inhibitor is highly effective, while either HSCT or immune checkpoint inhibitor treatment alone does not produce immunologic or clinical effects. The results demonstrate a previously undescribed and potent synergistic effect of HSC transfer on immune checkpoint inhibitor treatment to treat cancer. Without wishing to be bound by any theory of the disclosure, we provide insight into mechanism through demonstration that this combination leads to a sustained increase in IFNγ positive T cells within the tumor microenvironment. We propose that the novel synergistic combination of immune checkpoint inhibitors and HSC transfer (and/or HSC mobilization) have profound effects on anti-tumor immunity. Herein, it is proposed that the administration of HSCs into tumor bearing hosts together with one or more immune checkpoint inhibitors may lead to increased IFNγ secretion. Such treatment may be particularly useful in hosts bearing either subcutaneous, systemic, or intracranial tumors and in tumor bearing hosts that receive radiation or chemotherapy, as well as in hosts that do not receive radiation or chemotherapy. This disclosure supports a synergistic effect of the combination treatment using immune checkpoint inhibitors with HSCs and/or with an HSC mobilizing agent.

According to one aspect of the disclosure, a method is provided for treating a disease selected from cancer or an infectious disease comprising administering to a subject having the disease one or more immune checkpoint inhibitors, and administering to the subject hematopoietic stem cells, in amounts effective to treat the disease.

According to one aspect of the disclosure, a method is provided for treating a disease selected from cancer or an infectious disease comprising administering to a subject having the disease one or more immune checkpoint inhibitors, and administering a hematopoietic stem cell mobilizing agent, in amounts effective to treat the disease.

According to one aspect of the disclosure, a method is provided for treating a disease selected from cancer or an infectious disease in a subject receiving immune checkpoint inhibitor therapy for the disease, comprising administering to the subject hematopoietic stem cells in an amount which, in combination with the immune checkpoint inhibitor therapy, is effective to treat the disease.

According to one aspect of the disclosure, a method is provided for treating a disease selected from cancer or an infectious disease in a subject receiving hematopoietic stem cell transplantation therapy for the disease, comprising administering to the subject one or more immune checkpoint inhibitors in an amount which, in combination with the hematopoietic stem cell transplantation therapy, is effective to treat the disease.

In any of the foregoing aspects and following embodiments, the disease may be, for example, one that is resistant to monotherapy treatment with the one or more immune checkpoint inhibitors. In any of the foregoing aspects and following embodiments, the one or more immune checkpoint inhibitors are, for example, each an antagonist of programmed death 1 (PD-1), programmed death ligand 1 (PD-L), cytotoxic T-lymphocyte-associated antigen 4 (CTLA-4), V-domain Ig suppressor of T cell activation (VISTA), programmed death ligand 2 (PD-L2), indoleamine 2,3-dioxygenase (IDO), arginase, B7 family inhibitory ligand B7-H3, B7 family inhibitory ligand B7-H4, lymphocyte activation gene 3 (LAG3), 2B4, B and T lymphocyte attenuator (BTLA), T cell membrane protein 3 (TIM3; also known as HAVcr2), adenosine A2a receptor (A2aR), a killer inhibitory receptor, and/or signal transducer and activator of transcription (STAT)3. In particular embodiments, the one or more immune checkpoint inhibitors are each an antagonist of programmed death 1 (PD-1), an antagonist of programmed death ligand 1 (PD-L), an antagonist of cytotoxic T-lymphocyte-associated antigen 4 (CTLA-4), and/or an antagonist of V-domain Ig suppressor of T cell activation (VISTA).

In any of the foregoing aspects and embodiments, the PD-1 antagonist is, for example, an agent that binds to and antagonizes PD-1. Such agents can be, for example, a peptide that binds PD-1. Such agents can be a humanized antibody that selectively binds PD-1. In some embodiments, the humanized antibody that selectively binds PD-1 is nivolumab, pembrolizumab, pidilizumab. MEDI-0680, REGN2810, or AMP-224. In some embodiments, the humanized antibody that selectively binds PD-1 is nivolumab, pembrolizumab, or pidilizumab. In some embodiments, the antagonist is (i) an antisense molecule directed against PD-1, (ii) an adnectin directed against PD-1, (iii) a single stranded or double stranded RNAi inhibitor of PD-1, and/or (iv) a small molecule inhibitor of PD-1.

In any of the foregoing aspects and embodiments, the PD-L1 antagonist is, for example, an agent that binds to and antagonizes PD-L1. Such agents can be, for example, a peptide that binds PD-L. Such agents can be a humanized antibody that selectively binds PD-L1. In some embodiments, the humanized antibody that selectively binds PD-L1 is BMS-936559/MDX-1105, MPDL3280A/RG7446/atezolizumab, MSB0010718C/avelumab, or MEDI4736/durvalumab. In some embodiments, the antagonist is (i) an antisense molecule directed against PD-L1, (ii) an adnectin directed against PD-L1, (iii) a single stranded or double stranded RNAi inhibitor of PD-L1, or (iv) a small molecule inhibitor of PD-L1.

In any of the foregoing aspects and embodiments, the CTLA-4 antagonist is, for example, an agent that binds to and antagonizes CTLA-4. Such agents can be, for example, a peptide that binds CTLA-4. Such agents can be a humanized antibody that selectively binds CTLA-4. In some embodiments, the humanized antibody that selectively binds CTLA-4 is ipilimumab or tremelimumab. In some embodiments, the CTLA-4 antagonist is (i) an antisense molecule directed against CD80, CD86, and/or CTLA-4, (ii) an adnectin directed against CD80, CD86, and/or CTLA-4, (iii) a single stranded or double stranded RNAi inhibitor of CD80, CD86, and/or CTLA-4, or (iv) a small molecule inhibitor of CD80, CD86, or CTLA-4.

In any of the foregoing aspects and embodiments, the VISTA antagonist is, for example, an agent that binds to and antagonizes VISTA. Such agents can be, for example, a peptide. Such agents can be an inhibitory antibody directed to VISTA. In some embodiments, the agent that binds to and antagonizes VISTA is a humanized antibody. In some embodiments, the agent that binds to and antagonizes VISTA is (i) an antisense molecule directed against VISTA, (ii) an adnectin directed against VISTA, (iii) a single stranded or double stranded RNAi inhibitor of VISTA, or (iv) a small molecule inhibitor of VISTA.

In any of the foregoing embodiments, the immune checkpoint inhibitor is administered on different day than the hematopoietic stem cell transplantation or hematopoietic stem cell mobilization agent. In any of the foregoing embodiments, the immune checkpoint inhibitor is administered on the same day as the hematopoietic stem cell transplantation or the hematopoietic stem cell mobilization agent. In any of the foregoing embodiments, the immune checkpoint inhibitor is administered on a different day than the hematopoietic stem cell transplantation or mobilization agent, but within one day of, within five days of, within one week of, within eight days of, within two weeks of, within three weeks of, within one month of, within two months of, or within three months of the hematopoietic stem cell transplantation or mobilization agent.

In any of the foregoing embodiments, the immune checkpoint inhibitor is administered, for example, intravenously or subcutaneously.

In any of the foregoing embodiments, the method further comprises administering a hematopoietic stem cell mobilizing agent to the subject. In exemplary embodiments, the mobilizing agent is granulocyte-macrophage colony-stimulating factor (GM-CSF), granulocyte colony-stimulating factor (G-CSF), PEGylated G-CSF (pegfilgratism), lenogratism, a glycosylated form of G-CSF, C-X-C motif chemokine 2 (CXCL2), C-X-C chemokine receptor type 4 (CXCR-4), or plerixafor.

In any of the foregoing embodiments, the disease is, for example, cancer and the cancer is melanoma, squamous cell carcinoma, basal cell carcinoma, breast cancer, head and neck carcinoma, thyroid carcinoma, soft tissue sarcoma, bone sarcoma, testicular cancer, prostatic cancer, ovarian cancer, bladder cancer, skin cancer, brain cancer, glioblastoma, medulloblastoma, ependymoma, angiosarcoma, hemangiosarcoma, mast cell tumor, primary hepatic cancer, small cell lung cancer, non-small-cell lung cancer, pancreatic cancer, gastrointestinal cancer, renal cell carcinoma, hematopoietic neoplasia, lymphoma, mesothelioma, glioblastoma, low-grade glioma, high-grade glioma, pediatric brain cancer, medulloblastoma, or a metastatic cancer thereof.

In any of the foregoing embodiments, the cancer is a metastatic or refractory cancer of the brain, lung, breast, or melanoma. In any of the foregoing embodiments, the cancer is a metastatic brain cancer from non-small cell lung cancer, a metastatic brain cancer from melanoma, or a metastatic brain cancer from breast carcinoma. In any of the foregoing embodiments, the cancer is glioblastoma, low-grade glioma, high-grade glioma, pediatric brain cancer, or medulloblastoma.

In any of the foregoing embodiments, the disease is, for example, an infectious disease. In any of the foregoing embodiments, the infectious disease is a chronic infectious disease. In any of the foregoing embodiments, the infectious disease is any hepatitis, adenovirus, polyoma virus such as BK, human immunodeficiency virus (HIV), herpes simplex virus (HSV), respiratory syncytial virus (RSV), cytomegalovirus (CMV), Epstein-Barr virus (EBV), Influenza A, B, and/or C, vesicular stomatitis virus (VSV), vesicular stomatitis virus (VSV), *Staphylococcus* species including Methicillin-resistant *Staphylococcus aureus* (MRSA), *Streptococcus* species including *Streptococcus pneumonia*, or a post-transplant infection. In any of the foregoing embodiments, the infectious disease is Hepatitis A, Hepatitis B, or Hepatitis C.

In any of the foregoing embodiments, the source of hematopoietic stem cells is, for example, bone marrow, bone marrow lineage depleted cells (lin−), cKit+ purified lineage negative bone marrow derived cells, Sca+ purified lineage negative bone marrow derived cells, cKit+ Sca+ purified bone marrow derived cells, mobilized from host bone marrow using GM-CSF, G-CSF, mobilized from host bone marrow using AMD3100, Plerixafor, or the molecule 1,1′-[1,4-phenylenebis(methylene)]bis [1,4,8,11-tetraazacyclotetradecane], umbilical cord blood or cord-blood derived stem cells, human leukocyte antigen (HLA)-matched blood, mesenchymal stem cells derived from blood or marrow, hematopoietic stem cells differentiated from induced pluripotent stem cells, mobilized peripheral blood, peripheral blood, hematopoietic stem cell subsets including lin− cells purified with CCR2+ marker, lineage negative purified peripheral blood, or CD34+ enriched peripheral blood. In any of the foregoing embodiments, the source of hematopoietic stem cells is bone marrow, peripheral blood, umbilical cord blood, or induced pluripotent stem cells. In any of the foregoing embodiments, the source of hematopoietic stem cells is autologous. In some embodiments, the source of hematopoietic stem cells is allogeneic and the donor cells are HLA-matched to the recipient.

In any of the foregoing embodiments, a sample containing the hematopoietic stem cells is obtained from and optionally processed to expand the number of stem cells within the sample, in vitro, prior to administering to the subject the hematopoietic stem cells. In any of the foregoing embodiments, a sample containing the hematopoietic stem cells is obtained and optionally processed to increase the percentage of stem cells within the sample, in vitro, prior to administering to the subject the hematopoietic stem cells. The sample can be autologous or not. In any of the foregoing embodiments, at least 5, 10, 15, 20, 25, 30, 35, 40, 45, or 50 percent of the hematopoietic stem cells are CCR2 positive (CCR2+), CD34 positive (CD34+), and/or lineage negative (lin−) cells. In any of the foregoing embodiments, between 20% and 98%, inclusive, e.g., 20%, 25%, 30%, 35%, 40%, 45%, 50%, 55%, 60%, 65%, 70%, 75%, 80%, 85%, 90%, 91%, 92%, 93%, 94%, 95%, 96%, 97%, or 98% of the hematopoietic stem cells for administration to the subject are CCR2 positive (CCR2+), CD34 positive (CD34+), or lineage negative (lin−).

In any of the foregoing embodiments, the hematopoietic stem cells for administration to the subject are optionally enriched ex-vivo for CCR2 positive (CCR2+) cells, for CD34 positive (CD34+) cells and/or for lineage negative (lin−) cells prior to administration to the subject. In any of the foregoing embodiments, the hematopoietic stem cells are optionally processed ex-vivo to deplete CCR2 negative (CCR2−) cells before administration to the subject. In any of the foregoing embodiments, the hematopoietic stem cells are optionally selected for CCR2+, CD34+, and/or lin− cells prior to administration to the subject by flow cytometric analysis, microbead-based isolation, an adherence assay, and/or a ligand-based selection. In some embodiments, the cells are selected by the ligand-based selection, wherein the ligand is a CCR2 ligand known as CCL2.

In any of the foregoing embodiments, an effect of the treatment on the disease is assessed, for example, by measuring interferon gamma (IFNγ) secretion by T cells obtained from within a tumor microenvironment or tumor draining lymph nodes of the subject, wherein a synergistic effect is noted if the presence of IFNγ is increased with combination therapy.

In any of the foregoing embodiments, adoptive cell therapy (ACT) also can be administered to the subject. In any of the foregoing embodiments, the adoptive cell therapy (ACT) is administered to the subject close enough in time with at least one of the said treatments to enhance treatment of the disease.

In any of the foregoing embodiments, chemotherapy or radiation can be administered to the subject. In any of the foregoing embodiments, the chemotherapy or the radiation is administered to the subject close enough in time with at least one of the said treatments to enhance treatment of the disease. In such embodiments, the hematopoietic stem cells may be administered to the subject after completion of radiation treatment. In such embodiments, the hematopoietic stem cells may be administered to the subject after completion of chemotherapy treatment. In such embodiments, the hematopoietic stem cells may be administered to the subject within six weeks after completion of chemotherapy or radiation treatment. In such embodiments, the hematopoietic stem cells may be administered to the subject zero days, one day, two days, three days, four days, five days, six days, one week, two weeks, three weeks, four weeks, five weeks, or six weeks after completion of chemotherapy or radiation treatment. In such embodiments, the immune checkpoint inhibitor may be administered prior to, concurrently with, or after radiation or chemotherapy treatment. In such embodiments, an immune checkpoint inhibitor may be administered to the subject one day, one week, two weeks, three weeks, four weeks, five weeks, or six weeks after completion of chemotherapy or radiation treatment.

In any of the foregoing embodiments, the hematopoietic stem cells can be treated with one or more different cytokines before administration of the hematopoetic stem cells to the subject. In any of the foregoing embodiments, the hematopoictic stem cells can be administered to the subject concurrently with one or more different cytokines. In any of the foregoing embodiments, treatment of HSCs with one or more different cytokines may further enhance effects of combination treatment with immune checkpoint inhibitor therapy and hematopoictic stem cell transplantation therapy. In any of the foregoing embodiments, administration of HSCs to the subject concurrently with administration of one or more different cytokines may further enhance effects of combination treatment with immune checkpoint inhibitor therapy and hematopoietic stem cell transplantation therapy. In some embodiments, the one or more different cytokines are IFNγ, TNFα, GM-CSF, G-CSF, F13-ligand, IL-1β, IL-4, and/or IL-6. In any of the foregoing embodiments, the hematopoietic stem cells are treated with one or more cytokines on the same day as, 1 day before, 2 days before, 3 days before, 4 days before, or 5 days before administration of the HSCs to the subject. In any of the foregoing embodiments, the hematopoietic stem cells are treated with one or more cytokines for 1, 2, 3, 4, or 5 days, before administration of the HSCs to the subject.

According to one aspect of the disclosure, hematopoietic stem cells are provided for use in treating a subject having a cancer or infectious disease, wherein the subject is undergoing concurrent immune checkpoint inhibitor treatment with one or more immune checkpoint inhibitors.

According to one aspect of the disclosure, hematopoietic stem cells that are enriched for CCR2+, CD34+, and/or lin− cells are provided for use in treatment of a subject receiving treatment for a disease with one or more immune checkpoint inhibitors.

According to one aspect of the disclosure, hematopoietic stem cells that are substantially depleted of CCR2− cells are provided for use in treatment of a subject receiving treatment for a disease with one or more immune checkpoint inhibitors.

According to one aspect of the disclosure, an immune checkpoint inhibitor is provided for use in treating a subject having a cancer or infectious disease, wherein the subject is undergoing concurrent treatment with hematopoictic stem cells.

According to one aspect of the disclosure, an immune checkpoint inhibitor is provided for use in treating a subject having a cancer or infectious disease, wherein the subject is undergoing concurrent treatment with hematopoietic stem cell transplantation and/or a hematopoietic stem cell mobilizing agent.

In any of the foregoing aspects, the disease may be resistant to monotherapy treatment with the one or more immune checkpoint inhibitors.

In any of the foregoing aspects, more than one different immune checkpoint inhibitor can be used concurrently in combination with hematopoietic stem cells and/or a hematopoietic stem cell mobilizing agent for treatment of a subject having cancer or an infectious disease.

In any of the foregoing aspects, the immune checkpoint inhibitor is, for example, an antagonist of programmed death 1 (PD-1), programmed death ligand 1 (PD-L1), cytotoxic T-lymphocyte-associated antigen 4 (CTLA-4), V-domain Ig suppressor of T cell activation (VISTA), programmed death ligand 2 (PD-L2), indoleamine 2,3-dioxygenase (IDO), arginase, B7 family inhibitory ligand B7-H3, B7 family inhibitory ligand B7-H4, lymphocyte activation gene 3 (LAG3), 2B4, B and T lymphocyte attenuator (BTLA), T cell membrane protein 3 (TIM3), adenosine A2a receptor (A2aR), and/or a killer inhibitory receptor. In any of the foregoing aspects, the immune checkpoint inhibitor is an antagonist of programmed death 1 (PD-1), programmed death ligand 1 (PD-L), cytotoxic T-lymphocyte-associated antigen 4 (CTLA-4), and/or V-domain Ig suppressor of T cell activation (VISTA).

In some embodiments, the immune checkpoint inhibitor is a programmed death 1 (PD-1) antagonist. In some embodiments, the immune checkpoint inhibitor is a programmed death ligand 1 (PD-L1) antagonist. In some embodiments, the immune checkpoint inhibitor is a cytotoxic T-lymphocyte-associated antigen 4 (CTLA-4) antagonist. In some embodiments, the immune checkpoint inhibitor is a V-domain Ig suppressor of T cell activation (VISTA) antagonist.

The PD-1 antagonist can be, for example, an agent that binds to and antagonizes PD-1. In some embodiments, the agent that binds to and antagonizes PD-1 is a peptide that binds PD-1. In some embodiments, the agent that binds to and antagonizes PD-1 is a humanized antibody that selectively binds PD-1. In some embodiments, the humanized antibody that selectively binds PD-1 is nivolumab, pembrolizumab, pidilizumab, MEDI-0680, REGN2810, or AMP-224. In some embodiments, the humanized antibody that selectively binds PD-1 is nivolumab, pembrolizumab, or pidilizumab.

The PD-L1 antagonist can be, for example, an agent that binds to and antagonizes PD-L1. In some embodiments, the agent that binds to and antagonizes PD-L1 is a peptide that binds PD-L1. In some embodiments, the agent that binds to and antagonizes PD-L1 is a humanized antibody that selectively binds PD-L1. In some embodiments, the humanized antibody that selectively binds PD-L1 is BMS-936559/MDX-1105, MPDL3280A/RG7446/atezolizumab, MSB0010718C/avelumab, or MEDI4736/durvalumab.

The CTLA-4 antagonist can be, for example, an agent that binds to and antagonizes CTLA-4. In some embodiments, the agent that binds to and antagonizes CTLA-4 is a peptide that binds CTLA-4. In some embodiments, the agent that binds to and antagonizes CTLA-4 is a humanized antibody that selectively binds CTLA-4. In some embodiments, the humanized antibody that selectively binds CTLA-4 inhibitor is ipilimumab or tremelimumab. In some embodiments, the CTLA-4 antagonist is (i) an antisense molecule directed against CD80, CD86, and/or CTLA-4, (ii) an adnectin directed against CD80, CD86, and/or CTLA-4, (iii) a single stranded or double stranded RNAi inhibitor of CD80, CD86, and/or CTLA-4, or (iv) a small molecule inhibitor of CD80, CD86, or CTLA-4.

The VISTA antagonist can be, for example, an agent that binds to and antagonizes VISTA. In some embodiments, the agent that binds to and antagonizes VISTA is a peptide. In some embodiments, the agent that binds to and antagonizes VISTA is an inhibitory antibody directed to VISTA. In some embodiments, the agent that binds to and antagonizes VISTA is a humanized antibody. In some embodiments, the agent that binds to and antagonizes VISTA is (i) an antisense molecule directed against VISTA, (ii) an adnectin directed against VISTA, (iii) a single stranded or double stranded RNAi inhibitor of VISTA, or (iv) a small molecule inhibitor of VISTA.

In some embodiments, the immune checkpoint inhibitor is administered on different day than the hematopoietic stem cell transplantation or hematopoietic stem cell mobilization agent. In some embodiments, the immune checkpoint inhibitor is administered on the same day as the hematopoietic stem cell transplantation hematopoietic stem cell mobilization agent. In some embodiments, the immune checkpoint inhibitor is administered on a different day than the hematopoietic stem cell transplantation hematopoietic stem cell mobilization agent, but within one day of, within five days of, within one week of, within eight days of, within two weeks of, within three weeks of, within one month of, within two months of, or within three months of the hematopoietic stem cell transplantation or hematopoietic stem cell mobilization agent.

In some embodiments, the immune checkpoint inhibitor is administered intravenously or subcutaneously.

In any of the foregoing embodiments, the method optionally further comprises administering a hematopoietic stem cell mobilizing agent to the subject. In some embodiments, the mobilizing agent is granulocyte-macrophage colony-stimulating factor (GM-CSF), granulocyte colony-stimulating factor (G-CSF), PEGylated G-CSF (pegfilgratism), lenogratism, a glycosylated form of G-CSF, C-X-C motif chemokine 2 (CXCL2), C-X-C chemokine receptor type 4 (CXCR-4), or plerixafor.

In any of the foregoing embodiments, the disease is, for example, cancer and the cancer is melanoma, squamous cell carcinoma, basal cell carcinoma, breast cancer, head and neck carcinoma, thyroid carcinoma, soft tissue sarcoma, bone sarcoma, testicular cancer, prostatic cancer, ovarian cancer, bladder cancer, skin cancer, brain cancer, glioblastoma, medulloblastoma, ependymoma, angiosarcoma, hemangiosarcoma, mast cell tumor, primary hepatic cancer, small cell lung cancer, non-small-cell lung cancer, pancreatic cancer, gastrointestinal cancer, renal cell carcinoma, hematopoietic neoplasia, lymphoma, mesothelioma, glioblastoma, low-grade glioma, high-grade glioma, pediatric brain cancer, medulloblastoma, or a metastatic cancer thereof. In some embodiments, the cancer is a metastatic or refractory cancer of the brain, lung, breast, or melanoma. In some embodiments, the cancer is a metastatic brain cancer from non-small cell lung cancer, a metastatic brain cancer from melanoma, or a metastastic brain cancer from breast carcinoma. In some embodiments, the cancer is glioblastoma, low-grade glioma, high-grade glioma, pediatric brain cancer, or medulloblastoma.

In some embodiments, the disease is, for example, an infectious disease. In some embodiments, the infectious disease is a chronic infectious disease. In any of the foregoing embodiments, the infectious disease is any hepatitis, adenovirus, polyoma virus such as BK, human immunodeficiency virus (HIV), herpes simplex virus (HSV), respiratory syncytial virus (RSV), cytomegalovirus (CMV), Epstein-Barr virus (EBV), Influenza A, B, and/or C, vesicular stomatitis virus (VSV), vesicular stomatitis virus (VSV), *Staphylococcus* species including Methicillin-resistant *Staphylococcus aureus* (MRSA), *Streptococcus* species including *Streptococcus pneumonia*, or a post-transplant infection. In some embodiments, the infectious disease is Hepatitis A, Hepatitis B, or Hepatitis C.

In any of the foregoing embodiments, the source of hematopoietic stem cells is, for example, bone marrow, bone marrow lineage depleted cells (lin−), cKit+ purified lineage negative bone marrow derived cells, Sca+ purified lineage negative bone marrow derived cells, cKit+ Sca+ purified bone marrow derived cells, mobilized from host bone marrow using GM-CSF, G-CSF, mobilized from host bone marrow using AMD3100, Plerixafor, or the molecule 1,1'-[1,4-phenylenebis(methylene)]bis [1,4,8,11-tetraazacyclo-tetradecane], umbilical cord blood or cord-blood derived stem cells, human leukocyte antigen (HLA)-matched blood, mesenchymal stem cells derived from blood or marrow, hematopoietic stem cells differentiated from induced pluripotent stem cells, mobilized peripheral blood, peripheral blood, hematopoietic stem cell subsets including lin−cells purified with CCR2+ marker, lineage negative purified peripheral blood, or CD34+ enriched peripheral blood. In some embodiments, the source of hematopoietic stem cells is bone marrow, peripheral blood, umbilical cord blood, or induced pluripotent stem cells.

In any of the foregoing embodiments, the source of hematopoietic stem cells is autologous. In any of the foregoing embodiments, the source of hematopoietic stem cells is allogeneic and the donor cells are HLA-matched to the recipient.

In some embodiments, a sample containing the hematopoietic stem cells is obtained and processed to expand the number of stem cells within the sample, in vino, prior to administering to the subject the hematopoietic stem cells. In some embodiments, a sample containing the hematopoietic stem cells is obtained and processed to increase the percentage of stem cells within the sample, in vitro, prior to administering to the subject the hematopoietic stem cells. In some embodiments, at least 5, 10, 15, 20, 25, 30, 35, 40, 45, or 50 percent of the hematopoietic stem cells are CCR2 positive (CCR2+). CD34 positive (CD34+), and/or lineage negative (lin−) cells. In some embodiments, between 20% and 98%, inclusive, e.g., 20%, 25%, 30%, 35%, 40%, 45%, 50%, 55%, 60%, 65%, 70%, 75%, 80%, 85%, 90%, 91%, 92%, 93%, 94%, 95%, 96%, 97%, or 98% of the hematopoictic stem cells for administration to the subject are CCR2 positive (CCR2+), CD34 positive (CD34+), or lineage negative (lin−). In some embodiments, the hematopoietic stem cells for administration to the subject are enriched ex-vivo for CCR2 positive (CCR2+) cells, for CD34 positive (CD34+) cells and/or for lineage negative (lin−) cells prior to administration to the subject. In some embodiments, the hematopoietic stem cells are processed ex-vivo to deplete CCR2 negative (CCR2−) cells before administration to the subject. In some embodiments, the hematopoietic stem cells are selected for CCR2+, CD34+, and/or lin-cells prior to administration to the subject by flow cytometric analysis, microbead-based isolation, an adherence assay, and/or a ligand-based selection. In some embodiments, the cells are selected by the ligand-based selection, wherein the ligand is a CCR2 ligand known as CCL2.

In some embodiments, an effect of the treatment on the disease can be assessed by measuring interferon gamma (IFNγ) secretion by T cells obtained from within a tumor microenvironment or tumor draining lymph nodes of the subject, wherein a synergistic effect is noted if the presence of IFNγ is increased with combination therapy.

In any of the foregoing embodiments, adoptive cell therapy (ACT) can be optionally administered to the subject. In some embodiments, the adoptive cell therapy (ACT) is administered to the subject close enough in time with at least one of the said treatments to enhance treatment of the disease.

In any of the foregoing embodiments, chemotherapy or radiation may be administered to the subject. In some embodiments, the chemotherapy or the radiation is administered to the subject close enough in time with at least one of the said treatments to enhance treatment of the disease.

In any of the foregoing embodiments, the hematopoietic stem cells can be treated with one or more different cytokines before administration of the hematopoietic stem cells to the subject. In some embodiments, treatment of HSCs with one or more different cytokines may further enhance effects of combination treatment with immune checkpoint inhibitor therapy and hematopoietic stem cell transplantation therapy. In some embodiments, the one or more different cytokines are IFNγ, TNFα, IL-1β, and/or IL-6.

In one aspect of the disclosure, a method is provided for treating a subject comprising, administering a stem cell mobilizing agent to the subject, harvesting hematopoietic stem cells from the subject, enriching the harvested stem cells for CCR2 positive (CCR2+), CD34 positive (CD34+), or lineage negative (lin–) cells, optionally depleting the harvested stem cells or CCR2-cells, administering to the subject the enriched harvested stem cells, and administering to the subject an immune checkpoint inhibitor.

BRIEF DESCRIPTION OF THE DRAWINGS

FIG. 1A shows a real-time PCR array demonstrating that the mice that received HSC co-transfer had increased IFNγ relative to the mice that did not.

FIG. 1B shows analysis for IFNγ secretion by adoptively transferred tumor-specific T cells using flow cytometry. FIG. 1C shows quantification of the results in FIG. 1B using flow cytometry, confirming the observations of FIG. 1B.

FIG. 2C shows results of studies that were then conducted to determine if the combination of HSC and anti-PD-1 antibody led to demonstrated superior anti-tumor protection. C57BL/6 mice were given 10,000 astrocytoma cells intracranially. On day 3, mice received either intravenous injection of HSCs, intraperitoneal injection of anti-PD-1 antibody, or both. Groups were followed to humane endpoints. Mice that received anti-PD-1 and HSCs had 40% complete cures.

FIGS. 8A and 8B show the percent of interferon gamma (IFNγ) secreting cells of total CD3+ T cells in tumor microenvironment determined by flow cytometric analysis of yellow fluorescent protein (YFP)/IFNγ+/CD3+ lymphocytes within the tumor microenvironment in untreated mice and mice treated with HSC, anti-PD1, or both HSC and anti-PD1 (FIG. 8A) and quantification of the flow cytometric analysis (FIG. 8B).

DETAILED DESCRIPTION

Figure 1A:
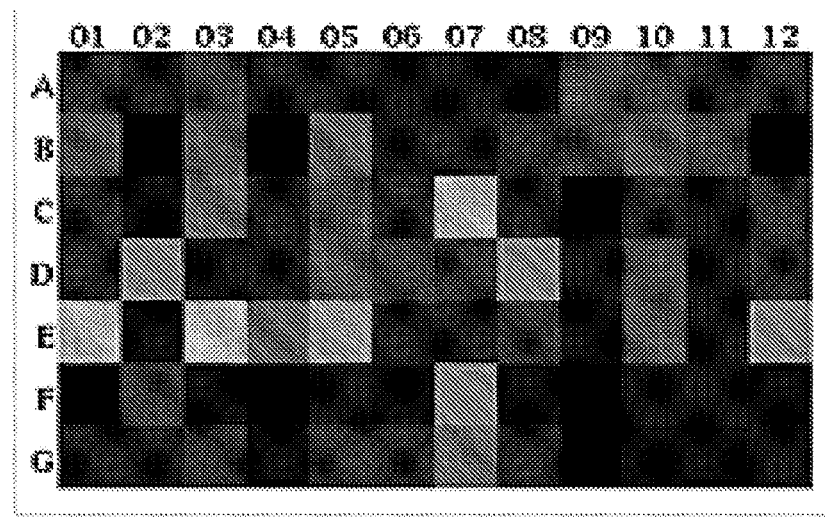
FIGS. 1A, 1B, and 1C show results of experiments on tumor bearing mice that received adoptive transfer of tumor-reactive T cells with or without HSC co-transfer. Tumor draining lymph nodes were dissected in both groups and analyzed for T cell activation.

The following detailed description is made by way of illustration of certain aspects of the disclosure. It is to be understood that other aspects are contemplated and may be made without departing from the scope or spirit of the present disclosure. The following detailed description, therefore, is not to be taken in a limiting sense. Scientific and technical terms used herein have meanings commonly used in the art unless otherwise specified. The definitions provided herein are to facilitate understanding of certain terms used frequently herein and are not meant to limit the scope of the present disclosure. The singular forms "a", "an", and "the" encompass the plural, unless the content clearly dictates otherwise. The term "or" is generally employed in its sense including "and/or" unless the content clearly dictates otherwise.

Cancer. The therapies described herein include treatment of an existing or established cancer, that is, one that exists and is detectable in the subject. Additionally, treatment of a precancerous lesion (i.e. adenomatous polyp, or cellular dysplasia) for the prevention of the development of cancer is envisioned. Cancers treatable according to the current disclosure include the following cancers: melanoma, squamous cell carcinoma, basal cell carcinoma, breast cancer, head and neck carcinoma, thyroid carcinoma, soft tissue sarcoma, bone sarcoma, testicular cancer, prostatic cancer, ovarian cancer, bladder cancer, skin cancer, brain cancer, glioblastoma, medulloblastoma, ependymoma, angiosarcoma, hemangiosarcoma, mast cell tumor, primary hepatic cancer, small cell lung cancer, non-small-cell lung cancer, pancreatic cancer, gastrointestinal cancer, renal cell carcinoma, hematopoietic neoplasia, lymphoma, mesothelioma, or a metastatic cancer thereof. In embodiments of the disclosure, the cancers to be treated in the disclosure include glioblastoma, low-grade glioma, high-grade glioma, brain stem glioma, cortical glioblastoma, pediatric brain cancer, and medulloblastoma. In embodiments of the disclosure, the cancer is invasive intracranial glioma. In embodiments of the disclosure, the cancer is a metastatic or refractory cancer of the brain, lung, breast, or melanoma. In embodiments of the disclosure, the cancer is a metastatic brain cancer from non-small cell lung cancer, a metastatic brain cancer from melanoma, or a metastastic brain cancer from breast carcinoma. In embodiments of the disclosure, the cancer is brain stem glioma, cortical glioblastoma, and medulloblastoma.

Infectious Disease. The disclosure also is useful in connection with the treatment of infectious disease. In general, opportunistic pathogenic microorganism may be categorized as virus, fungus, parasite, and bacterium. Illustrative pathogenic viral organisms causing human diseases include (but are not restricted to) Filoviruses, Herpes viruses, Hepatitis viruses, Retroviruses, Human Immunodeficiency Virus (HIV), orthomyxoviruses, Paramyxoviruses, Togaviruses, Picornaviruses, Papovaviruses and Gastroenteritisviruses. Illustrative pathogenic bacteria causing serious human diseases are the Gram positive organisms: *Staphylococcus aureus, Staphylococcus epidermidis, Enterococcus faecalis* and *E. faecium, Streptococcus pneumoniae* and the Gram negative organisms: *Pseudomonas aeruginosa, Burkholdia cepacia, Xanthomonas maltophila, Escherichia coli, Enterobacter* spp, *Klebsiella pneumoniae* and *Salmonella* spp. Illustrative pathogenic protozoan organisms causing human diseases include (but are not restricted to) Malaria e.g. *Plasmodium falciparum* and *M. ovale*, Trypanosomiasis (sleeping sickness) e.g. *Trypanosoma cruzei*, Leishmaniasis e.g. Leishmania *donovani*, Amebiasis e.g. *Entamoeba histolytica*. Illustrative pathogenic fungi causing or associated with human diseases include (but are not restricted to) *Candida albicans, Histoplasma neoformans, Coccidioides immitis* and *Penicillium marneffei*. In embodiments, the infectious disease organism is one involved in chronic infectious disease. Particularly important diseases are hepatitis, adenovirus, polyoma virus such as BK, human immunodeficiency virus (HIV), herpes simplex virus (HSV), respiratory syncytial virus (RSV), cytomegalovirus (CMV), Epstein-Barr virus (EBV), Influenza A, B, and C, vesicular stomatitis virus (VSV), vesicular stomatitis virus (VSV), *Staphylococcus* species including Methicillin-resistant *Staphylococcus aureus* (MRSA), *Streptococcus* species including *Streptococcus pneumonia*, and post-transplant infection.

Antibodies. An antibody, or immunoglobulin, is a glycoprotein containing two identical light chains (L chains), each containing approximately 200 amino acids, and two identical heavy chains (H chains), which generally are at least twice as long as the L chains. The paratope of the antibody is specific for a particular epitope of an antigen, and their spacial complementarity (binding) "tags" the microbe for further action or neutralize its actions directly. The antibody communicates with other components of the immune response via its crystallizable fragment (Fc) region, which includes a conserved glycosylation site. There are five Fc regions, resulting in the five different antibody isotypes: IgA, IgD, IgE, IgG, and IgM. IgD functions as an antigen receptor on B cells that have not been exposed to antigens, and activates bosophils and mast cells, resulting in the production of antimicrobial factors. IgG, expressed in four forms, provides the majority of antibody-based immunity against invading pathogens. IgM is expressed on the surface of B cells as a monomer, and in a secreted form as a pentamer. It eliminates pathogens during the early phases of humoral (B cell-mediated) immunity before there are sufficient levels of IgG. IgG is often used in immunotherapy.

The term antibody is used in the broadest sense and specifically includes, for example, single monoclonal antibodies, antibody compositions with polyepitopic specificity, single chain antibodies, and antigen-binding fragments of antibodies. An antibody may include an immunoglobulin constant domain from any immunoglobulin, such as IgG1, IgG2, IgG3, or IgG4 subtypes, IgA (including IgA1 and IgA2), IgE, IgD or IgM.

In some embodiments, the antibodies and other therapeutic molecules used herein may be isolated. Isolated means, in the context of an antibody or other biologic, the antibody or other biologic has been removed from its natural milieu or has been altered from its natural state. As such, isolated does not necessarily reflect the extent to which the molecule has been removed from its natural milieu or has been altered from its natural state. However, it will be understood that an antibody or other biologic that has been purified to some degree and to an extent to which it can be used for its intended therapeutic purpose is "isolated".

The antibodies used herein are humanized. Humanized forms of non-human (e.g., murine) antibodies are chimeric immunoglobulins (including full length immunoglobulins), immunoglobulin chains or fragments thereof (such as Fv, Fab, Fab', F(ab')2, scFv or other antigen-binding subsequences of antibodies) which contain minimal sequence derived from the non-human immunoglobulin. Humanized antibodies typically include human immunoglobulins (recipient antibody) in which residues from a complementary determining region (CDR) of the recipient are replaced by residues from a CDR of a non-human species (donor antibody) such as mouse, rat, or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992)). Modifications to the Fc region of antibodies are well established, including modifications to cause the antibody to lose its complement dependent cytotoxicity properties and modifications to enhance the antibody's ability to cross cell membranes.

The antibodies used herein selectively bind their targets, specifically Programmed Death 1 (PD-1), Programmed Death Ligand-1 (PD-L), cytotoxic T-lymphocyte-associated antigen (CTLA)-4, V-domain Ig suppressor of T cell activation (VISTA or PD-L3), programmed death ligand 2 (PD-L2), indoleamine 2,3-dioxygenase (IDO), arginase (ARG1), B7 family inhibitory ligand B7-H3, B7 family inhibitory ligand B7-H4, lymphocyte activation gene 3 (LAG3; also known as CD223), 2B4 (also known as CD244), B and T lymphocyte attenuator (BTLA; also known as CD272), T cell membrane protein 3 (TIM3; also known as HAVcr2), adenosine A2a receptor (A2aR), or a member of the family of killer inhibitory receptors, e.g., killer cell immunoglobulin-like receptors (KIRs) and C-type lectin receptors. PD-L1 is a ligand of PD-1. CTLA-4 functions as an immune checkpoint molecule, as does PD-1. VISTA is an Ig superfamily inhibitory ligand that has some homology (~25% by sequence homology) in its extracellular domain to PD-L1.

Aspects of the disclosure relate to using or administering one or more immune checkpoint inhibitors that can bind to and/or antagonize an immune checkpoint molecule, e.g., PD-1, PD-L1, CTLA-4, VISTA, PD-L2, IDO, ARG1, B7-H3, B7-H4, LAG3, 2B4, BTLA, TIM3, A2aR, and/or a KIR. An agent that selectively binds to an immune checkpoint molecule without limitation can be, e.g., an antibody or an antigen-binding fragment thereof, a protein or peptide, a small molecule, or a nucleic acid. An immune checkpoint molecule that is a nucleic acid can be, e.g., an antisense molecule, a single- or double-stranded DNA oligonucleotide, a single- or double-stranded RNA oligonucleotide, a peptide nucleic acid (PNA), a single- or double-stranded RNAi molecule, an shRNA, or an siRNA. A small molecule is an organic compound drug. An agent that selectively binds to an immune checkpoint molecule can bind to nucleic acids or amino acids of the immune checkpoint molecule sequence. An agent that selectively binds an immune checkpoint molecule can bind to any region of the immune checkpoint molecule.

Immune Checkpoints. Immune checkpoints refer to inhibitory pathways hardwired into the immune system that are crucial for maintaining self-tolerance and modulating the duration and amplitude of physiological immune responses in peripheral tissues in order to minimize collateral tissue damage. Immune checkpoint molecules can be stimulatory or inhibitory to an immune checkpoint. The present disclosure and claims refer to inhibitory molecules of immune checkpoints as "immune checkpoint molecules". Preliminary clinical findings with agents that block immune checkpoint molecules (e.g., PD1 or CTLA-4), suggest opportunities to enhance antitumor immunity with the potential to produce effective clinical responses. The present application discloses that combining immune checkpoint blockade using immune checkpoint inhibitor(s) with HSCT and/or HSC mobilization treatment enhances treatment efficacy in a subject having a cancer or an infectious disease.

Immune Checkpoint inhibitors and Immune Checkpoint Blockade. An immune checkpoint inhibitor is a type of drug that blocks the signaling of immune checkpoint molecule(s) made by some types of immune system cells, such as T cells and some cancer cells. Immune checkpoint inhibitors therefore can cause immune checkpoint blockade. Immune checkpoint molecules (e.g., PD1) help keep immune responses in check and can keep T cells from killing cancer cells. When these molecules are blocked, the "brakes" on the immune system are released (inhibition of the immune system is reduced or blocked) and T cells are able to kill cancer cells better. Examples of checkpoint proteins found on T cells or cancer cells include PD-1/PD-L1 and CTLA-4. In some embodiments, immune checkpoint molecules are proteins. In some embodiments, immune checkpoint molecules are nucleic acids that encode the proteins. In some embodiments, immune checkpoint inhibitors bind to and/or antagonize immune checkpoint molecules. In some embodiments, immune checkpoint inhibitors are used in combination with hematopoietic stem cell transplantation and/or hematopoietic stem cell mobilizing agent treatment to treat a subject having cancer. In some embodiments, immune checkpoint inhibitors are used in combination with hematopoietic stem cell transplantation and/or hematopoietic stem cell mobilizing agent treatment to treat a subject having an infectious disease.

As mentioned, according to the present invention, immune checkpoint blockade is used in combination therapy with hematopoietic stem cell (HSC) transplantation/transfer and/or HSC mobilization. In some embodiments, a method for treating a disease or a subject having a disease comprises administering the HSCs and/or HSC mobilization agent and administering an agent that binds to and/or antagonizes programmed death 1 (PD-1), programmed death ligand 1 (PD-L1), cytotoxic T-lymphocyte-associated Antigen 4 (CTLA-4), and/or V-domain Ig suppressor of T cell activation (VISTA). The disclosure is not limited to targeting PD-1, PD-L1, CTLA-4, and/or VISTA for immune checkpoint blockade. Other inhibitory checkpoint molecules may be targeted by immune checkpoint inhibitors in combination therapy with HSC transplantation and/or HSC mobilization, e.g., without limitation, agents that bind to and/or antagonize programmed death ligand 2 (PD-L2), indoleamine 2,3-dioxygenase (IDO), arginase (ARG1), B7 family inhibitory ligand B7-H3, B7 family inhibitory ligand B7-H4, lymphocyte activation gene 3 (LAG3; also known as CD223), 2B4 (also known as CD244), B and T lymphocyte attenuator (BTLA; also known as CD272), T cell membrane protein 3 (TIM3; also known as HAVcr2), adenosine A2a receptor (A2aR), a member of the family of killer inhibitory receptors (KIRs), e.g., killer cell immunoglobulin-like receptors (KIRs) and C-type lectin receptors, and signal transducer and activator of transcription (STAT3). In some embodiments, the immune checkpoint molecule is e.g., PD-1, PD-L1, CTLA-4, VISTA, PD-L2, IDO, ARG1, B7-H3, B7-H4, LAG3, 2B4, BTLA, TIM3, A2aR, STAT3, or a KIR. The agent that binds to and/or antagonizes an immune checkpoint molecule is an immune checkpoint inhibitor.

One or more immune checkpoint inhibitors. One or more immune checkpoint inhibitors refers to one or more different inhibitors. Each different inhibitor has a different molecule structure. Two different inhibitors may bind the same immune checkpoint molecule or each may bind a different immune checkpoint molecule.

An inhibitor or antagonist, as used herein, is a molecule that inhibits, reduces, or blocks activity of an immune checkpoint molecule to inhibit a suppressive effect that the immune checkpoint molecule has on the immune system. The inhibitor or antagonist can directly bind the immune checkpoint molecule, a molecule controlling the expression of the immune checkpoint molecule, or a ligand of the immune checkpoint molecule that mediates the activity of the immune checkpoint molecule. The inhibitor or antagonist may be an antibody (including a humanized antibody), a small molecule, a peptide, or a nucleic acid (e.g., an antisense molecule, or a single- or double-stranded RNAi molecule). Activity of the immune checkpoint molecule is referred to as its suppressive effect on an immune checkpoint. An immune checkpoint inhibitor can reduce or block the activity of an immune checkpoint molecule.

Exemplary Immune Checkpoint Molecules and Antagonists.

Programmed Death 1 (PD-1). In humans, programmed cell death protein 1 (PD-1) is encoded by the PDCD1 gene. PDCD1 has also been designated as CD279 (cluster of differentiation 279). This gene encodes a cell surface membrane protein of the immunoglobulin superfamily. PD-1 is a 288 amino acid cell surface protein molecule. PD-1 is expressed on the surface of activated T cells, B cells, and macrophages. PD-1 is expressed in pro-B cells and is thought to play a role in their differentiation. See T. Shinohara et al., Genomics 23 (3): 704-6 (1995). PD-1 is a member of the extended CD28CTLA-4 family of T cell regulators. (Y. Ishida et al., "EMBO J. 11 (11): 3887-95, (1992)). PD-1 may negatively regulate immune responses. PD1 limits autoimmunity and the activity of T cells in peripheral tissues at the time of an inflammatory response to infection.

PD-1 has two ligands, PD-L1 and PD-L2, which are members of the B7 family. PD-L1 protein is upregulated on macrophages and dendritic cells (DC) in response to LPS and GM-CSF treatment, and on T cells and B cells upon TCR and B cell receptor signaling, whereas in resting mice, PD-L1 mRNA can be detected in the heart, lung, thymus, spleen, and kidney. PD-L1 is expressed on almost all murine tumor cell lines, including PA myeloma, PH815 mastocytoma, and B16 melanoma upon treatment with IFN-γ. PD-L1 has been found to be highly expressed by several cancers and several PD-1 antagonists are being developed or are approved for treatment of cancer. PD-L2 expression is more restricted and is expressed mainly by DCs and a few tumor lines.

Programmed Death 1 (PD-1) antagonist. A PD-1 antagonist, as used herein is a molecule that binds to PD-1 protein or to a gene or nucleic acid encoding PD-1 protein and inhibits or prevents PD-1 activation. Without wishing to be bound by theory, it is believed that such molecules reduce or block the interaction of PD-1 with its ligand(s) PD-L1 and/or PD-L2. In some embodiments, a PD-1 antagonist may reduce PD-1 activity in a cell or organism more when combined with HSCT and/or HSC mobilizing agent treatment, than when administered alone, as compared to a cell or organism that has not been exposed to the PD-1 antagonist.

PD-1 activity may be interfered with by antibodies that bind selectively to and block the activity of PD-1. The activity of PD-1 can also be inhibited or blocked by molecules other than antibodies that bind PD-1. Such molecules can be small molecules or can be peptide mimetics of PD-L1 and PD-L2 that bind PD-1 but do not activate PD-1. Molecules that antagonize PD-1 activity include those described in U.S. Publications 20130280265, 20130237580, 20130230514, 20130109843, 20130108651, 20130017199, and 20120251537, 2011/0271358, EP 2170959B1, the entire disclosures of which are incorporated herein by reference. See also M. A. Curran, et al., Proc. Natl. Acad. Sci. USA 107, 4275 (2010); S. L. Topalian, et al., New Engl. J. Med. 366, 2443 (2012); J. R. Brahmer, et al., New Engl. J. Med. 366, 2455 (2012); and D. E. Dolan et al., Cancer Control 21, 3 (2014), all incorporated by reference herein, in their entireties. Herein, exemplary PD-1 antagonists include: nivolumab, also known as BMS-936558, OPDIVO® (Bristol-Meyers Squibb, and also known as MDX-1106 or ONO-4538), a fully human IgG4 monoclonal antibody against PD-1; pidilizumab, also known as CT-011 (CureTech), a humanized IgG1 monoclonal antibody that binds PD-1; MK-3475 (Merck, and also known as SCH 900475), an IgG4 antibody that binds PD-1; and pembrolizumab (Merck, also known as MK-3475, lambrolizumab, or KEYTRUDA®), a humanized IgG4-kappa monoclonal antibody that binds PD-1; MEDI-0680 (AstraZeneca/MedImmune), a monoclonal antibody that binds PD-1; and REGN2810 (Regeneron/Sanofi), a monoclonal antibody that binds PD-1. Another exemplary PD-1 antagonist is AMP-224 (Glaxo Smith Kline and Amplimmune), a recombinant fusion protein composed of the extracellular domain of the PD-1 ligand programmed cell death ligand 2 (PD-L2) and the Fc region of human IgG1, that binds to PD-1. Agents that interfere bind to the DNA or mRNA encoding PD-1 also can act as PD-1 inhibitors. Examples include a small inhibitory anti-PD-1 RNAi, an anti-PD-1 antisense RNA, or a dominant negative protein. PDL-2 fusion protein AMP-224 (co-developed by Glaxo Smith Kline and Amplimmune) is believed to bind to and block PD-1. In some embodiments, anti-PD-1 antibodies may be used for treatment in combination with hematopoietic stem cell (HSC) transfer and/or HSC mobilization in further combination with additional immune checkpoint blockade, e.g., with anti-PD-L, anti-CTLA-4, and/or anti-VISTA treatment.

Programmed Death-Ligand 1 (PD-L1). In humans, programmed death-ligand 1 (PD-L), also known as B7 homolog 1 (B7-H1) or cluster of differentiation 274 (CD274), is a 40 kDa type 1 transmembrane protein that is encoded by the CD274 gene. Foreign antigens normally induce an immune response triggering proliferation of antigen-specific T cells, such as antigen-specific CD8+ T cells. PD-L1 is an immune checkpoint inhibitor that may block or lower such an immune response. PD-L1 may play a major role in suppressing the immune system during events such as pregnancy, tissue allografts, autoimmune disease, and other disease states, such as hepatitis and cancer. The PD-L1 ligand binds to its receptor, PD-1, found on activated T cells, B cells, and myeloid cells, thereby modulating activation or inhibition. In addition to PD-1, PD-L1 also has an affinity for the costimulatory molecule CD80 (B7-1). Upon IFN-T stimulation, PD-L1 is expressed on T cells, natural killer (NK) cells, macrophages, myeloid dendritic cells (DCs), B cells, epithelial cells, and vascular endothelial cells.

PD-L1 Antagonist. A PD-L1 antagonist, as used herein, is a molecule that binds to PD-L1 protein or to a gene or nucleic acid encoding PD-L protein and inhibits or prevents PD-1 activation. Without wishing to be bound by theory, it is believed that such molecules reduce or block the interaction of PD-L1 with PD-1. PD-L1 activity may be blocked by molecules that selectively bind to and block the activity of PD-L1. In some embodiments, a PD-L1 antagonist may reduce PD-L1 activity in a cell or organism more when combined with HSCT and/or HSC mobilizing agent treatment, than when administered alone, as compared to a cell or organism that has not been exposed to the PD-1 antagonist. Anti-PD-L antibodies block interactions between PD-L1 and both PD-1 and B7-1 (also known as CD80). Block means inhibit or prevent the transmission of an inhibitory signal mediated via such PD-L1 binding. PD-L1 antagonists include, for example: BMS-936559, also known as MDX-1105 (Bristol-Meyers Squibb), a fully human, high affinity, immunoglobulin (Ig) G4 monoclonal antibody to PD-L; MPDL3280A, also known as RG7446 or atezolizumab (Genentech/Roche), an engineered human monoclonal antibody targeting PD-L1; MSB0010718C, also known as avelumab (Merck), a fully human IgG1 monoclonal antibody that binds to PD-L1; and MEDI473 (AstraZeneca/MedImmune), a human immunoglobulin (Ig) G1κ monoclonal antibody that blocks PD-L1 binding to its receptors. Agents that bind to the DNA or mRNA encoding PD-L1 also can act as PD-L inhibitors, e.g., small inhibitory anti-PD-L1 RNAi, small inhibitory anti-PD-L1 RNA, anti-PD-L1 antisense RNA, or dominant negative PD-L1 protein. Antagonists of or agents that antagonize PD-L1, e.g., anti-PD-L1 antibodies and PD-L1 antagonists, may include, but are not limited to those previously mentioned and any of those that are disclosed in Stewart et al., 2015, 3(9):1052-62; Herbst et al., 2014, Nature Volume: 515:Pages: 563-567; Brahmer et al., N Engl J Med 2012; 366:2455-2465; U.S. Pat. No. 8,168,179; US20150320859; and/or US20130309250, all incorporated herein by reference. In clinical trials, treatment with anti-PD-L1 antibodies resulted in less adverse events than did treatment with anti-PD-1 antibodies (Shih et al., 2014). In some embodiments, anti-PD-L1 antibodies may be used for treatment in combination with hematopoietic stem cell (HSC) transfer and/or HSC mobilization in further combination with additional immune checkpoint blockade, e.g., with anti-PD-1, anti-CTLA-4, and/or anti-VISTA treatment.

Cytotoxic T-Lymphocyte-Associated Antigen 4 (CTLA-4). CTLA-4 (also known as CTLA-4 or cluster of differentiation 152 (CD152)), is a transmembrane glycoprotein that, in humans, is encoded by the CTLA-4 gene. CTLA-4 is a member of the immunoglobulin superfamily, which is expressed on the surface of helper T cells and is present in regulatory T cells, where it may be important for immune function. CTLA-4, like the homologous CD28, binds to B7 molecules, particularly CD80/B7-1 and CD86/B7-2 on antigen-presenting cells (APCs), thereby sending an inhibitory signal to T cells. CTLA-4 functions as an immune checkpoint that inhibits the immune system and is important for maintenance of immune tolerance.

CTLA-4 antagonist. A CTLA-4 antagonist, as used herein, is a molecule that binds to CTLA-4 protein or to a gene or nucleic acid encoding CTLA-4 protein and inhibits or prevents CTLA-4 activation. Without wishing to be bound by theory, it is believed that such molecules reduce or block the interaction of CTLA-4 with its ligands, e.g., B7 molecules CD80/B7-1 and CD86/B7-2. CTLA-4 activity may be blocked by molecules that bind selectively to and block the activity of CTLA-4 or that bind selectively to its counter-receptors, e.g., CD80, CD86, etc. and block activity of CTLA-4. Blocking means inhibit or prevent the transmission of an inhibitory signal via CTLA-4. In some embodiments, anti-CTLA-4 antibodies may be used for treatment in combination with hematopoietic stem cell (HSC) transfer and/or HSC mobilization in further combination with additional immune checkpoint blockade, e.g., with anti-PD-1, anti-PD-L1, and/or anti-VISTA treatment.

CTLA-4 antagonists include, for example, inhibitory antibodies directed to CD80, CD86, and/or CTLA-4; small molecule inhibitors of CD80, CD86, and CTLA-4; antisense molecules directed against CD80, CD86, and/or CTLA-4; adnectins directed against CD80, CD86, and/or CTLA-4; and RNAi inhibitors (both single and double stranded) of CD80, CD86, and/or CTLA-4.

Suitable CTLA-4 antagonists and/or anti-CTLA-4 antibodies include humanized anti-CTLA-4 antibodies, such as MDX-010/ipilimumab (Bristol-Meyers Squibb), tremelimumab/CP-675,206 (Pfizer; AstraZeneca), and antibodies that are disclosed in PCT Publication No. WO 2001/014424, PCT Publication No. WO 2004/035607, U.S. Publication No. 2005/0201994, European Patent No. EP 1212422 B1, U.S. Pat. Nos. 5,811,097, 5,855,887, 6,051,227, 6,984,720, 7,034,121, 8,475,790, U.S. Publication Nos. 2002/0039581 and/or 2002/086014, the entire disclosures of which are incorporated herein by reference. Other anti-CTLA-4 antibodies and/or CTLA-4 antagonists that can be used in a method of the present disclosure include, for example, those disclosed in Hurwitz et al., Proc. Natl. Acad. Sci. USA, 95(17):10067-10071 (1998); Camacho et al., J. Clin. Oncology, 22(145): Abstract No. 2505 (2004) (antibody CP-675206); Mokyr et al., Cancer Res., 58:5301-5304 (1998), and Lipson and Drake, Clin Cancer Res; 17(22) Nov. 15, 2011; U.S. Pat. No. 8,318,916; and/or EP1212422B1, all of which are herein incorporated by reference, in their entireties.

V-domain Ig suppressor of T cell activation (VISTA). V-domain Ig suppressor of T cell activation (VISTA), (also known as PD-H1, PD-1 homolog, or Dies1), is a negative regulator of T cell function. VISTA is a 309 aa type I transmembrane protein that is composed of seven exons, it has one Ig-V like domain, and its sequence is similar to the Ig-V domains of members of CD28 and B7 families. VISTA is highly expressed in the tumor microenvironment (TME) and on hematopoietic cells. It is also expressed on macrophages, dendritic cells, neutrophils, natural killer cells, and naive and activated T cells. Its expression is highly regulated on myeloid antigen-presenting cells (APCs) and T cells, while lower levels are found on CD4$^+$ T cells, CD8$^+$ T cells, and T$^{reg}$ cells. VISTA shows some sequence homology to the PD-1 ligand, PD-L1, however the two immune checkpoint inhibitors are structurally different and have different signaling pathways. VISTA blockade has been shown to enhance antitumor immune responses in mice, while in humans, blockade of the related PD-1 pathway has shown great potential in clinical immunotherapy trials. VISTA is a negative checkpoint regulator that suppresses T-cell activation and its blockade may be an efficacious immunotherapeutic strategy for human cancer. (Wang et al., 2011. JEM. 208(3):577-92; Lines et al., 2014. Cancer Res. 74(7):1924-32; Kondo et al. 2015. J. of Immuno. V194; WO2011120013; US20140105912; US20140220012; US20130177557, US20130177557, incorporated by reference herein, in their entireties).

VISTA Antagonist. A VISTA antagonist, as used herein, is a molecule that binds to VISTA protein or to a gene or nucleic acid encoding VISTA protein and inhibits or prevents VISTA activation. Without wishing to be bound by theory, it is believed that such molecules reduce or block the interaction of VISTA with its ligand(s). VISTA activity may be blocked by molecules that selectively bind to and block the activity of VISTA. Molecules or agents that are VISTA antagonists include peptides that bind VISTA, antisense molecules directed against VISTA, single- or double-stranded RNAi molecules targeted to degrade or inhibit VISTA, small molecule inhibitors of VISTA, anti-VISTA antibodies, inhibitory antibodies directed to VISTA, and humanized antibodies that selectively bind and inhibit VISTA. Antagonists of or agents that antagonize VISTA, e.g., anti-VISTA antibodies and VISTA antagonists, are not limited to, but may include any of those that are disclosed in Liu et al. 2015. PNAS. 112(21):6682-6687; Wang et al., 2011. JEM. 208(3):577-92; Lines et al., 2014. Cancer Res. 74(7):1924-32; Kondo et al. 2015. J. of Immuno. V194; WO2015097536, EP2552947, WO2011120013, US20140056892, U.S. Pat. No. 8,236,304, WO2014039983, US20140105912, US20140220012, US20130177557; WO2015191881; US20140341920; CN105246507; and/or US20130177557, all of which are incorporated by reference herein, in their entireties. In some embodiments, anti-VISTA antibodies may be used for treatment in combination with hematopoietic stem cell (HSC) transfer and/or HSC mobilization in further combination with additional immune checkpoint blockade, e.g., with anti-PD-1, anti-PD-L1, and/or anti-CTLA-4 treatment.

Other Immune Inhibitory Molecules and Immune Checkpoint Inhibitors. Molecules other than PD-1, PD-L1, CTLA-4, and VISTA may be targeted by one or more immune checkpoint inhibitors/agents that bind to and/or antagonize immune checkpoint molecule(s), in combination with hematopoietic stem cell and/or hematopoietic stem cell mobilizing agent treatments. In some embodiments, the one or more immune checkpoint inhibitors are each an antagonist of PD-1, PD-L1, CTLA-4, VISTA, PD-L2, IDO, ARG1, B7-H3, B7-H4, LAG3, 2B4, BTLA, TIM3, A2aR, KIR, and/or STAT3.

Programmed Death Ligand 2 (PD-L2). Human PD-L2, also known as B7 dendritic cell molecule B7-DC, Btdc, PD-1 ligand 2, PD-1-ligand 2, PDCD1 ligand 2, butyrophilin B7-DC, and bA574F11.2, is a protein that is encoded by the PDCD1LG2 gene (also known as cluster of differentiation 273/CD273). PD-L2 is an principally an inhibitory molecule that is expressed by antigen-presenting cells, T cells and other immune cells, and even some nonimmune cells in an inducible manner, mainly through Th2-associated cytokines. See Rozali et al., Clinical and Developmental Immunology, 2012 (2012) for review. Engagement of PD-1 by PD-L2 dramatically inhibits T cell receptor (TCR)-mediated proliferation and cytokine production by CD4$^+$ T cells. At low antigen concentrations, PD-L2-PD-1 interactions inhibit strong B7-CD28 signals. In contrast, at high antigen concentrations, PD-L2-PD-1 interactions reduce cytokine production but do not inhibit T cell proliferation (Latchman et al., Nature immunology, 2(3):261-268 (2001)).

A PD-L2 antagonist, as used herein, is a molecule that binds to PD-L2 protein or to a gene or nucleic acid encoding PD-L2 protein and inhibits or prevents PD-L2 activation. Without wishing to be bound by theory, it is believed that such molecules reduce or block the interaction of PD-L2 with its ligand(s), e.g., PD-1.

Indoleamine 2,3-Dioxygenase (IDO). IDO, also known as INDO and IDO-1, is a gene that encodes indoleamine 2,3-dioxygenase (IDO)—a heme enzyme that catalyzes the first and rate-limiting step in tryptophan catabolism to N-formyl-kynurenine. IDO it is a cytosolic metabolic enzyme that is an immune inhibitory molecule which is expressed by tumor cells and infiltrating myeloid cells. The IDO enzyme is overexpressed by a variety of tumor cell types and antigen presenting cells (APCs) and is responsible for tryptophan catabolism and conversion of tryptophan into kynurenine. This enzyme acts on multiple tryptophan substrates including D-tryptophan, L-tryptophan, 5-hydroxy-tryptophan, tryptamine, and serotonin. This enzyme is thought to play a role in a variety of pathophysiological processes such as antimicrobial and antitumor defense, neuropathology, immunoregulation, and antioxidant activity. Through its expression in dendritic cells, monocytes, and macrophages this enzyme modulates T-cell behavior by its per cellular catabolization of the essential amino acid tryptophan. The IDO enzyme can be inhibited to enhance intratumoral inflammation by molecular analogues of its substrate(s) that act as competitive inhibitors or suicide substrates. Activation of the immune system, which is suppressed in many cancers, may induce a cytotoxic T-lymphocyte (CTL) response against the IDO1-expressing tumor cells. Tryptophan depletion inhibits T-lymphocyte proliferation and activation and is associated with immunosuppression caused by T-cell suppression.

An IDO antagonist, as used herein, is a molecule that binds to IDO protein or to a gene or nucleic acid encoding IDO protein and inhibits or prevents IDO activation. Without wishing to be bound by theory, it is believed that such molecules reduce or block the activity of DO. Exemplary IDO antagonists, e.g., are IDO inhibitor epacadostat, NLG919, and indoleamine 2,3-dioxygenase peptide vaccine.

Epacadostat is an orally available hydroxyamidine and inhibitor of indoleamine 2,3-dioxygenase (IDO1), with potential immunomodulating and antineoplastic activities. Epacadostat targets and binds to IDO, an enzyme responsible for the oxidation of tryptophan into kynurenine. By inhibiting IDO1 and decreasing kynurenine in tumor cells, epacadostat increases and restores the proliferation and activation of various immune cells, including dendritic cells (DCs), NK cells, and T-lymphocytes, as well as interferon (IFN) production, and a reduction in tumor-associated regulatory T cells (Tregs).

NLG919 is an orally available inhibitor of indoleamine 2,3-dioxygenase 1 (IDO1), with potential immunomodulating and antineoplastic activities. Upon administration, NLG919 targets and binds to IDO1, a cytosolic enzyme responsible for the oxidation of the essential amino acid tryptophan into kynurenine. By inhibiting IDO1 and decreasing kynurenine in tumor cells, this 7.9 agent increases tryptophan levels, restores the proliferation and activation of various immune cells, including dendritic cells (DCs), natural killer (NK) cells, T-lymphocytes, and causes a reduction in tumor-associated regulatory T-cells (Tregs).

Indoleamine 2,3-dioxygenase peptide vaccine is a peptide vaccine against the immunomodulatory enzyme indoleamine 2,3-dioxygenase (IDO), with potential immunomodulating and antineoplastic activities. Vaccination with indoleamine 2,3-dioxygenase peptide vaccine may activate the immune system to induce an immune response against IDO-expressing cells. This may increase and restore the proliferation and activation of various immune cells, including dendritic cells (DCs), natural killer (NK) cells, and T-lymphocytes, and may eradicate IDO-expressing tumor cells.

Arginase (ARG1). ARG1 is another metabolic enzyme that is an immune inhibitory molecule. It is produced by myeloid-derived suppressor cells. Arginase catalyzes the hydrolysis of arginine to ornithine and urea. At least two isoforms of mammalian arginase exist (types I and II) which differ in their tissue distribution, subcellular localization, immunologic cross-reactivity, and physiologic function. The type I isoform encoded by this gene, is a cytosolic enzyme and expressed predominantly in the liver as a component of the urea cycle. Inherited deficiency of this enzyme results in argininemia, an autosomal recessive disorder characterized by hyperammonemia. Two transcript variants encoding different isoforms have been found for this gene.

An ARG1 antagonist, as used herein, is a molecule that binds to ARG1 protein or to a gene or nucleic acid encoding ARG1 protein and inhibits or prevents ARG1 activation. Without wishing to be bound by theory, it is believed that such molecules reduce or block the activity of ARG1. The arginase enzyme can be inhibited to enhance intrauromal inflammation by molecular analogues of its substrate(s) that act as competitive inhibitors or suicide substrates. B7 Family Inhibitory Ligands B7-H3 and B7-H4. B7 family members and their known ligands belong to the immunoglobulin superfamily. The B7 family has co-stimulatory and inhibitory receptors. Numerous B7 family inhibitory ligands, e.g., B7-H3 (also known as CD276) and B7-H4 (also known as B7-S1, B7x and VCTN1), do not yet have defined receptors, but mouse knockout experiments support an immune inhibitory role for these ligands. B7-H3 and B7-H4 are upregulated on tumor cells or tumor-infiltrating cells. B7-H3 may be upregulated on endothelial cells of the tumor vasculature, and B7-H4 has been reported to be expressed on tumor-associated macrophages. B7-H4 is expressed by tumor cells and tumor-associated macrophages and plays a role in tumor escape. Preclinical mouse models of cancer have shown that blockade of many individual immune-checkpoint B7 family ligands or receptors can enhance antitumor immunity, and dual blockade of coordinately expressed receptors can produce additive or synergistic antitumor activities. Inhibitors/antagonists for a number of these immune-checkpoint targets are either entering the clinic or are under active development.

A B7 family member antagonist, as used herein, is a molecule that binds to a B7 family member protein or to a gene or nucleic acid encoding a B7 family member protein and inhibits or prevents activation of the B7 family member. Without wishing to be bound by theory, it is believed that such molecules reduce or block the interaction of a B7 family member, e.g., B7-H3 or B7-H4, with its ligand(s). Exemplary B7-H3 antagonists include e.g., Enoblituzumab (MacroGenics, also known as MGA271), an Fc-optimized monoclonal antibody that targets B7-H3, and MGD009, a Dual-Affinity Re-Targeting (DART®) molecule targeting B7-H3 and CD3 (MacroGenics). Blocking antibodies or small molecule inhibitors are currently available for, e.g., LAG3, 2B4, BTLA, TIM3, A2aR, and the family of killer inhibitory receptors, molecules which may be targeted by agents that bind to and/or antagonize them in the context of this disclosure.

Lymphocyte Activation Gene 3 (LAG3). LAG3 (also known as CD233) belongs to the immunoglobulin superfamily (IgSF) and contains 4 extracellular Ig-like domains. It binds to major histocompatibility complex (MHC) class II. LAG-3 expression on tumor infiltrating lymphocytes (TILs) is associated with tumor-mediated immune suppression. LAG3 has been shown to have a role in enhancing the function of $T_{Reg}$ cells. LAG3 inhibits CD8+ effector T cell functions independently of its role on $T_{Reg}$ cells. A known ligand for LAG3 is major histocompatibility complex (MHC) class H. MHC class II molecules are upregulated on some epithelial cancers, generally in response to IFNγ, and are expressed on tumor-infiltrating macrophages and dendritic cells. The role of the LAG3-MHC class II interaction in the LAG3-mediated inhibition of T cell responses is unclear because LAG3 antibodies that do not block the LAG3-MHC class II interaction nonetheless enhance T cell proliferation and effector cell functions in vitro and in vivo. This interaction may be most important for the role of LAG3 in enhancing $T_{Reg}$ cell function. LAG3 is one of various immune-checkpoint receptors that are coordinately upregulated on both $T_{Reg}$ cells and anergic T cells, and simultaneous blockade of these receptors can result in enhanced reversal of this anergic state relative to blockade of one receptor alone. In particular, PD1 and LAG3 are commonly co-expressed on anergic or exhausted T cells. Dual blockade of LAG3 and PD synergistically reversed anergy among tumor-specific CD8+ T cells and virus-specific CD8+ T cells in the setting of chronic infection.

A LAG3 antagonist, as used herein, is a molecule that binds to LAG3 protein or to a gene or nucleic acid encoding LAG3 protein and inhibits or prevents LAG3 activation. Without wishing to be bound by theory, it is believed that such molecules reduce or block the interaction of LAG3 with its ligand(s). An exemplary LAG3 antagonist is BMS-986016 (Bristol-Myers Squibb), a monoclonal antibody that binds LAG-3 with potential immune checkpoint inhibitory and antineoplastic activities. Upon administration, BMS-986016 binds to LAG-3 on tumor infiltrating lymphocytes (TILs). This may activate antigen-specific T-lymphocytes and enhance cytotoxic T cell-mediated tumor cell lysis, which leads to a reduction in tumor growth.2B4. 2B4 (also known as CD244 and SLAMf4) is a 38-kD type I transmembrane protein and member of the CD2 subset of the immunoglobulin superfamily molecules (Lee et al., 2004; Vaidya et al., 2005). It is encoded by a gene (2B4) that encodes a cell surface receptor expressed on natural killer (NK) cells, and some T cells, that mediate non-major histocompatibility complex (MHC) restricted killing. The interaction between NK-cell and target cells via the 2B4 receptor is thought to modulate NK-cell cytolytic activity. 2B4 is a co-inhibitory molecule identified as being expressed on exhausted cells after chronic viral infection. It is expressed on NK cells, monocytes, basophils, and eosinophils, and is inducibly expressed on a subset of CD8+ T cells in both mice and humans (see Liu et al., JEM, 211(2):297-311 (2014) and references within). Alternatively spliced transcript variants encoding different isoforms have been found for the human 2B4 gene.

B and T Lymphocyte Attenuator (BTLA). BTLA (also known as B and T Lymphocyte Associated, BTLA-1, and CD272) is a gene that encodes a member of the immunoglobulin superfamily. The encoded protein contains a single immunoglobulin (Ig) domain and is a receptor that relays inhibitory signals to suppress the immune response. Alternative splicing results in multiple transcript variants. Polymorphisms in this gene have been associated with an increased risk of rheumatoid arthritis. BTLA was first identified as an inhibitory receptor on T cells on the basis of the enhanced T cell responses that were observed in Btla-knockout mice. Subsequently, herpesvirus entry mediator (HVEM; also known as TNFRSF14), which is expressed on certain tumor cell types (e.g., melanoma) and on tumor-associated endothelial cells, was shown to be the BTLA ligand. This is a rare case in which a TNF family member interacts with an immunoglobulin supergene family member. BTLA expression levels on activated virus-specific CD8+ T cells are quite low, but can be much higher on tumor infiltrating lymphocytes (TILs) from patients with melanoma. $BTLA^{hi}$ T cells are inhibited in the presence of its ligand, HVEM. Thus, BTLA may be a relevant inhibitory receptor for T cells in the tumor microenvironment.

A BTLA antagonist, as used herein, is a molecule that binds to BTLA protein or to a gene or nucleic acid encoding BTLA protein and inhibits or prevents BTLA activation. Without wishing to be bound by theory, it is believed that such molecules reduce or block the interaction of BTLA with its ligand(s).

T Cell Membrane Protein 3 (TIM3). The TIM3 (also known as Hepatitis A Virus Cellular Receptor 2/HAVcr2, CD366, KIM-3, TIMD3, Tim-3, and TIMD-3) gene encodes a protein belonging to the immunoglobulin superfamily and TIM family of proteins. CD4-positive T helper lymphocytes can be divided into types 1 (Th1) and 2 (Th2) on the basis of their cytokine secretion patterns. Th1 cells are involved in cell-mediated immunity to intracellular pathogens and delayed-type hypersensitivity reactions, whereas, Th2 cells are involved in the control of extracellular helminthic infections and the promotion of atopic and allergic diseases. The TIM3 protein is a Th1-specific cell surface protein that regulates macrophage activation, and inhibits Th1-mediated auto- and alloimmune responses, and promotes immunological tolerance. TIM3, the ligand of which is galectin 9 (a galectin that is upregulated in various types of cancer, including breast cancers) inhibits T helper 1 (TH1) cell responses, and TIM3 antibodies enhance antitumor immunity. TIM3 has been reported to be co-expressed with PD1 on tumor-specific CD8+ T cells, and dual blockade of both molecules significantly enhances the in vitro proliferation and cytokine production of human T cells when stimulated by the cancer-testes antigen, NY-ESO-1. In animal models, coordinate blockade of PD1 and TIM3 was reported to enhance antitumor immune responses and tumor rejection in circumstances in which only modest effects from blockade of each individual molecule were observed.

A TIM3 antagonist, as used herein, is a molecule that binds to TIM3 protein or to a gene or nucleic acid encoding TIM3 protein and inhibits or prevents TIM3 activation. Without wishing to be bound by theory, it is believed that such molecules reduce or block the interaction of TIM3 with its ligand(s).

Adenosine A2a Receptor (A2aR). The A2aR gene (also known as RDC8 and ADORA2) encodes a member of the guanine nucleotide-binding protein (G protein)-coupled receptor (GPCR) superfamily, which is subdivided into classes and subtypes. The receptors are seven-pass transmembrane proteins that respond to extracellular cues and activate intracellular signal transduction pathways. A2AR is a G protein-coupled receptor which is highly expressed on the cell surfaces of T-cells and, upon activation by adenosinc, inhibits their proliferation and activation. Adenosine is often produced in excess by cancer cells. The A2aR protein, an adenosine (ligand) receptor of A2A subtype, uses adenosine as the preferred endogenous agonist and preferentially interacts with the G(s) and G(olf) family of G proteins to increase intracellular cAMP levels. It plays an important role in many biological functions, such as cardiac rhythm and circulation, cerebral and renal blood flow, immune function, pain regulation, and sleep. It has been implicated in pathophysiological conditions such as inflammatory diseases and neurodegenerative disorders. Alternative splicing results in multiple transcript variants. A read-through transcript composed of the upstream SPECC1L (sperm antigen with calponin homology and coiled-coil domains 1-like) and ADORA2A (adenosine A2a receptor) gene sequence has been identified, but it is thought to be non-coding. A2aR inhibits T cell responses, in part by driving CD4+ T cells to express FOXP3 and hence to develop into T cells. Deletion of this receptor results in enhanced and sometimes pathological inflammatory responses to infection. The A2aR receptor is particularly relevant to tumor immunity because the rate of cell death in tumors from cell turnover is high, and dying cells release adenosine. In addition, $T_{Reg}$ express high levels of the exoenzymes CD39 (also known as NTP-Dase 1), which converts extracellular ATP to AMP, and CD73 (also known as 5'-NT), which converts AMP to adenosine. Given that A2aR engagement by adenosine drives T cells to become $T_{Reg}$ cells, this can produce a self-amplifying loop within the tumor. Tumors grow more slowly in A2aR (also known as Adora2a)-knockout mice, and tumor vaccines are much more effective against established tumors in these mice.

An A2aR antagonist, as used herein, is a molecule that binds to A2aR protein or to a gene or nucleic acid encoding A2aR protein and inhibits or prevents A2aR activation. Without wishing to be bound by theory, it is believed that such molecules reduce or block the interaction of A2aR with its ligand(s). A2aR can be inhibited either by antibodies that block adenosine binding or by adenosine analogues, some of which are fairly specific for A2aR. Although these drugs have been used in clinical trials for Parkinson's disease, they have not yet been tested clinically in patients with cancer. An exemplary A2aR antagonist, without limitation, is adenosine A2A receptor antagonist PBF-509. PBF-509 is an orally bioavailable adenosine A2A receptor (A2AR) antagonist, with potential antineoplastic activity. Upon administration, A2AR antagonist PBF-509 selectively binds to and inhibits A2AR expressed on T lymphocytes. This abrogates the adenosine/A2AR-mediated inhibition of T-lymphocytes and activates a T-cell-mediated immune response against tumor cells, thereby reducing proliferation of susceptible tumor cells.

Killer Inhibitory Receptor (KIR). KIR, a member of the immunoglobulin superfamily, is expressed on the surface of NK cells. Killer cell immunoglobulin-like receptors (KIRs) are transmembrane glycoproteins expressed by natural killer cells and subsets of T cells. The KIR genes are polymorphic and highly homologous and they are found in a cluster on chromosome 19q13.4 within the 1 Mb leukocyte receptor complex (LRC). The gene content of the KIR gene cluster varies among haplotypes, although several "framework" genes are found in all haplotypes (KIR3DL3, KIR3 DPI, KIR3DL4, KIR3DL2). The KIR proteins are classified by the number of extracellular immunoglobulin domains (2D or 3D) and by whether they have a long (L) or short (S) cytoplasmic domain. KIR proteins with the long cytoplasmic domain transduce inhibitory signals upon ligand binding via an immune tyrosine-based inhibitory motif (ITIM), while KIR proteins with the short cytoplasmic domain lack the ITIM motif and instead associate with the TYRO protein tyrosine kinase binding protein to transduce activating signals. KIRs are a broad category of inhibitory receptors that can be divided into two classes based on structure: killer cell immunoglobulin-like receptors (KIRs) and C-type lectin receptors, which are type II transmembrane receptors. These receptors were originally described as crucial regulators of the killing activity of NK cells, although many are expressed on T cells and APCs. The importance of their inhibitory role on T cells and APCs (for example, dendritic cells) is less well studied but the resulting activation of NK cells can provide potent antitumor activity. Many of the killer inhibitory receptors are specific for subsets of human leukocyte antigens (HLAs; the human MHC molecules) and possess allele-specificity. However, other receptors recognize broadly expressed molecules; for example, the C-type lectin receptor KLRG1 recognizes E-cadherin. The potential value of NK cells in antitumor immune responses when their inhibitory receptors are not appropriately engaged is best exemplified by the significantly enhanced graft-versus-tumor effects in allogeneic bone marrow transplants elicited by mismatches between donor NK inhibitory receptors and recipient HLA alleles. The ligands for several KIR proteins are subsets of HLA class I molecules; thus, KIR proteins are thought to play an important role in regulation of the immune response. An antagonist of any killer inhibitory receptor may be used in the context of the disclosure.

A KIR antagonist, as used herein, is a molecule that binds to KIR protein or to a gene or nucleic acid encoding KIR protein and inhibits or prevents KIR activation. Without wishing to be bound by theory, it is believed that such molecules reduce or block the interaction of KIR with its ligand(s). An exemplary KIR antagonist is Lirilumab (Bristol-Myers Squibb), a fully humanized monoclonal antibody against killer-cell immunoglobulin-like receptors (KIR), with potential immune checkpoint inhibitory and antineoplastic activities. Upon administration, lirilumab binds to KIR, thereby preventing the binding of KIR ligands to KIR on natural killer (NK) cells. By blocking these inhibitory receptors, NK cells become activated and attack cancer cells leading to tumor cell death.

Signal transducer and activator of transcription (STAT3). The protein encoded by the STAT3 gene is a member of the STAT protein family. In response to cytokines and growth factors, STAT family members are phosphorylated by the receptor associated kinases, and then form homo- or heterodimers that translocate to the cell nucleus where they act as transcription activators. Seven members of the STAT family of proteins have been identified in mammalians: STAT1, 2, 3, 4, 5a, 5b, and 6. All of the family members share six distinct structural domains, including the N-terminal, coiled-coil, DNA-binding, Src homology 2 (SH2), and the transactivation domains, and contain a critical tyrosine (Tyr) residue at the C-terminus (Tyr705 for STAT3), which is phosphorylated during activation. The STAT3 protein is activated through phosphorylation in response to various cytokines and growth factors including IFNs, EGF, IL5, IL6, HGF, LIF and BMP2. This protein mediates the expression of a variety of genes in response to cell stimuli, and thus plays a key role in many cellular processes such as cell growth and apoptosis. The small GTPase Rac1 has been shown to bind and regulate the activity of this protein. PIAS3 protein is a specific inhibitor of this protein. Mutations in this gene are associated with infantile-onset multi-system autoimmune disease and hyper-immunoglobulin E syndrome. Alternative splicing results in multiple transcript variants encoding distinct isoforms.

A STAT3 antagonist, as used herein, is a molecule that binds to STAT3 protein or to a gene or nucleic acid encoding STAT3 protein and inhibits or prevents STAT3 activation. Without wishing to be bound by theory, it is believed that such molecules reduce or block the interaction of STAT3 with its ligand(s). Examples of small molecule compounds that are antagonists of STAT3 are NSC 74859 (S3I-201), NSC 42067, NSC 59263, NSC 75912, NSC 11421, NSC 91529, and NSC 263435 (see U.S. Pat. No. 7,960,434 B2). Many other examples of STAT3 inhibitors/antagonists can be found in Yue and Turkson, *Expert Opin Investig Drugs*, 2009, 18(1):45-56, incorporated herein by reference.

Antagonists of the inhibitory immune checkpoint molecules described may be used in the context of this disclosure. Antagonists of other molecules that are inhibitory immune molecules may be used in the context of this disclosure. In some embodiments, an antagonist of any immune inhibitory molecule may be used in combination with the use of hematopoictic stem cells and/or a hematopoietic stem cell mobilizing agent for treatment of a subject having a disease, wherein the disease is a cancer or an infectious disease. In some embodiments, an antagonist of PD-1, PD-L1, CTLA-4, VISTA, PD-L2. IDO, ARG1, B7-H3, B7-H4, LAG3, 2B4, BTLA, TIM3, A2aR, KIR, and/or STAT3 may be used for treatment in combination with hematopoietic stem cell (HSC) transfer and/or HSC mobilization treatment in further combination with additional immune checkpoint blockade, e.g., with anti-PD-1, anti-PD-L1, anti-CTLA-4, and/or anti-VISTA treatment.

Hematopoietic Stem Cell. A hematopoietic stem cell (HSC), also called a blood stem cell, is an immature cell found in the blood and the bone marrow that can renew itself, and that can differentiate into a variety of specialized cells, such as blood and immune cells, including white blood cells, red blood cells, and platelets. HSCs can mobilize out of the bone marrow into circulating blood. HSCs facilitate constant renewal of blood cells, producing billions of new blood cells each day.

Hematopoietic Stem Cell Transplantation (HSCT). Hematopoietic stem cell (HSC) transplantation (HSCT or HSC transfer) is the transplantation of HSCs, usually derived from peripheral blood, bone marrow, or umbilical cord blood. Two types of HSCT may be used in a subject: autologous stem cell transplantation, wherein the subject's own stem cells are used, or allogenic stem cell transplantation, wherein a donor's stem cells, that are genetically similar and HLA-matched to the recipient, are transplanted into the subject. In some embodiments of the disclosure, autologous stem cells are used for HSCT. In some embodiments of the disclosure, allogeneic stem cells that are HLA-matched to the subject are used for HSCT. In autologous HSCT, a sample containing stem cells are removed from the subject, stored, and later transplanted back into the subject.

HSCs represent a small fraction of the total population of blood cells in the sample, so it may be advantageous to increase the number of autologous or allogeneic HSCs before administering them to the subject for cancer or infectious disease therapy. In some embodiments of the disclosure, hematopoietic stem cells are collected and expanded, before transplanting them into the subject for treatment. In some embodiments of the disclosure, hematopoietic stem cells are collected, expanded, and selected for from the sample, before transplanting them into the subject for treatment. In some embodiments, a sample containing the hematopoictic stem cells is obtained and processed to expand the number of stem cells within the sample, in vitro, prior to administering to the subject the hematopoietic stem cells. In some embodiments, a sample containing the hematopoictic stem cells is obtained and processed to increase the percentage of stem cells within the sample, in vitro, prior to administering to the subject the hematopoietic stem cells.

In embodiments, stem cells can be enriched in the material used for transplantation. In embodiments, the enrichment can occur by selectively stimulating the growth/expansion of stem cells versus other cells collected from a subject. In another embodiment, the stem cells can be enriched by isolating stem cells from other cells collected from a subject. Such selection may be so-called positive selection or negative selection. In positive selection, stem cells are isolated based on markers known to be on stem cells but not on other cells. In some embodiments, in positive selection, stem cells are isolated based on the markers CCR2+, CD34+, and/or lin-, thereby enriching the HSCs for the positive marker(s). In negative selection, cells that are not stem cells are identified and removed based on markers on such other cells, leaving behind stem cells. In some embodiments, in negative selection, stem cells are isolated based on the marker CCR2-. In the negative selection, the HSCs are processed ex-vivo to deplete the CCR2– cells thereby enriching the HSCs for the positive marker(s) CCR2+, CD34+, and/or lin– before administering the HSCs to the subject. Such selection procedures are well known to those of ordinary skill in the art and include but are not limited to flow cytometric analysis, microbead-based isolation, adherence assays, and/or a ligand-based selection. In some embodiments, the ligand-based selection, is based on the presence of a CCR2 ligand, e.g., CCL2. In some embodiments, the enriched HSCs may be proliferated in vitro before administration to the subject. In some embodiments, the enriched HSCs may be proliferated in vitro, and again positively selected for CCR2+, CD34+, and/or lin-, before administration to the subject. In some embodiments, the enriched HSCs may be proliferated in vitro, and negatively selected for CCR2-cells, wherein the CCR2– cells are again depleted before administering the HSCs to the subject. In some embodiments, after depletion of the CCR2– cells, less than 20/of starting population of CCR2– HSCs remain. In some embodiments, after depletion of the CCR2– cells, less than 15%, 10%, 5%, less than 2% and even less than 1% of starting population of CCR2– HSCs remain. In some embodiments, depleting CCR2– cells before administration of the HSCs to the subject results in HSCs for administration that contain no more than 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, or 80% CCR2– HSCs. In some embodiments, after positive selection for CCR2+, CD34+, and/or lin-cells; after positive selection for CCR2+, CD34+, and/or lin– cells and proliferation of the positively selected cells; or after positive selection for CCR2+, CD34+, and/or lin– cells, proliferation of the positively selected cells, and a second positive selection for CCR2+, CD34+, and/or lin– cells, and before administration of the HSCs, the HSCs for administration contain at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, or 98% CCR2+, CD34+, and/or lin– HSCs.

Sources of hematopoietic stem cells herein include: bone marrow lineage depleted cells (lin–), cKit+ purified lineage negative bone marrow derived cells, Sca+ purified lineage negative bone marrow derived cells, cKit+ Sca+ purified bone marrow derived cells, mobilized from host bone marrow using G-CSF, mobilized from host bone marrow using AMD3100, Plerixafor, or the molecule 1,1'-[1,4-phenylenebis(methylene)]bis [1,4,8,11-tetraazacyclotetradecane], umbilical cord blood or cord-blood derived stem cells, human leukocyte antigen (HLA)-matched blood, mesenchymal stem cells derived from blood or marrow, hematopoietic stem cells differentiated from induced pluripotent stem cells, mobilized peripheral blood, peripheral blood, hematopoietic stem cell subsets including Lin– cells purified with CCR2+ marker, lineage negative purified peripheral blood, or CD34+ enriched peripheral blood. In some embodiments of the disclosure, the source of HSCs is bone marrow. In some embodiments of the disclosure, the source of HSCs is autologous or allogeneic, optionally wherein, the source is bone marrow, peripheral blood, umbilical cord blood, umbilical cord blood stem cells, or induced pluripotent stem cells.

Hematopoietic Stem Cell Mobilizing Agent. In some embodiments of the disclosure, a hematopoietic stem cell mobilizing agent is administered to the subject. HSC mobilization refers to the recruitment of HSCs from the bone marrow of a subject into the peripheral blood of the subject. In the current application, HSC mobilizing agents include: granulocyte colony-stimulating factor (G-CSF), PEGylated G-CSF (pegfilgratism), lenogratism, a glycosylated form of G-CSF, C-X-C motif chemokine 2 (CXCL2), C-X-C chemokine receptor type 4 (CXCR-4), and plerixafor.

Combination Treatment or Combination Therapy. Combination treatment or therapy refers to two therapies combined. The combination may be as a single dosage form, but more typically will be in separate dosages with separate dosing regimens. In embodiments, combination therapy may refer to immune checkpoint inhibitor therapy combined with hematopoietic stem cell transplantation therapy and/or hematopoietic stem cell mobilizing agent treatment. Immune checkpoint inhibitor therapy refers to treatment of a subject having a disease (e.g., a cancer or an infectious disease) with administration of one or more immune checkpoint inhibitors to the subject. Hematopoietic stem cell transplantation therapy refers to treatment of a subject having a disease (e.g., a cancer or an infectious disease) with administration of hematopoietic stem cells. This may be combined with administration of a hematopoietic stem cell mobilizing agent to the subject. The hematopoietic stem cells may be proliferated, pre-selected based on markers, treated with cytokines, and/or administered with cytokines, as disclosed herein, before administration to the subject. In some embodiments, the subject is concurrently undergoing chemotherapy and/or radiation treatment, which are both commonly known methods in the art, with the immune checkpoint inhibitor and hematopoietic stem cell transplantation combination therapies. In such embodiments, the hematopoietic stem cells may be administered to the subject after completion of radiation treatment. In such embodiments, the hematopoietic stem cells may be administered to the subject after completion of chemotherapy treatment. In such embodiments, the hematopoietic stem cells may be administered to the subject within six weeks after completion of chemotherapy or radiation treatment. In such embodiments, the hematopoietic stem cells may be administered to the subject zero days, one day, two days, three days, four days, five days, six days, one week, two weeks, three weeks, four weeks, five weeks, or six weeks after completion of chemotherapy or radiation treatment. In such embodiments, the immune checkpoint inhibitor may be administered prior to, concurrently with, or after radiation or chemotherapy treatment. In such embodiments, an immune checkpoint inhibitor may be administered to the subject one day, one week, two weeks, three weeks, four weeks, five weeks, or six weeks after completion of chemotherapy or radiation treatment.

Monotherapy Treatment. Monotherapy treatment refers to treatment with one or more immune checkpoint inhibitors without hematopoietic stem cell transplantation treatment and/or hematopoietic stem cell mobilizing agent treatment.

Subject. "Subject" means a mammal, such as a human, a nonhuman primate, a dog, a cat, a sheep, a horse, a cow, a pig, a mouse, a rat, a rodent, or a goat. In an important embodiment, the subject and/or mammal is a human.

Treatment. "Treat", "treating", "treatment", and "therapy" encompass an action that occurs while a subject is suffering from a condition which reduces the severity of the condition (or a symptom associated with the condition) or retards or slows the progression of the condition (or a symptom associated with the condition). This is therapeutic treatment.

Effective Amount. Subjects are treated with effective amounts of the solutions of the disclosure. An "effective amount" of an agent generally refers to an amount sufficient to elicit the desired biological response, i.e., treat the condition. As will be appreciated by those of ordinary skill in the art, the effective amount of an agent described herein may vary depending on such factors as the condition being treated, the mode of administration, and the age, body composition, and health of the subject.

For therapeutic treatment, an effective amount is an amount sufficient to provide a therapeutic benefit in the treatment of a condition or to reduce or eliminate one or more symptoms associated with the condition. This may encompass an amount that improves overall therapy, reduces or avoids symptoms or causes of the condition, or enhances the therapeutic efficacy of another therapeutic agent.

In general, effective amounts are administered to enhance an immune response in the subject. In connection with a specific disease or condition, "enhance an immune response" means to halt the development of, inhibit the progression of, reverse the development of, or otherwise reduce or ameliorate one or more symptoms of the disease or condition, for example, one or more symptoms of cancer or one or more symptoms of an infectious disease. In addition, effective amounts may be such amounts which slow, halt or reverse the growth of cancer cells or an infectious disease agent in the subject.

An exemplary effective amount of hematopoietic stem cells for injection is about $2 \times 10^6$ cells per kilogram (kg) body weight of the subject. Exemplary effective amounts of hematopoietic stem cells for injection can range above and below this amount. Examples include from about 1, 1.5, 2, 2.5, 3, 3.5, 4, 4.5, 5, 5.5, 6, 6.5, or $7 \times 10^6$ cells/kg.

Exemplary effective amounts of agents as used in the art range as follows:

Anti-immune checkpoint antibodies: 0.01 mg/kg to 20 mg/kg every 1-4 weeks. In embodiments, such administration is for so long as the cancer or infectious disease persists. In embodiments, the administration can be, for example, up to 156 weeks.

Anti-PD-1 Antibodies: 0.01 mg/kg to 20 mg/kg every 1-4 weeks. In embodiments, such administration is for so long as the cancer or infectious disease persists. In embodiments, the administration can be, for example, up to 156 weeks. In embodiments, pembrolizumab can be administered at 10 mg/kg every two weeks, 10 mg/kg every three weeks, or 2 mg/kg every three weeks, for example, up to 96 weeks;

nivolumab can be administered at 0.1 to 10 mg/kg every two weeks for example, up to 96 weeks; pidilizumab can be administered at 0.1 to 10 mg/kg every one week, 0.1 to 10 mg/kg every two weeks, or 0.1 to 10 mg/kg every three weeks, for example, up to 96 weeks. In embodiments, MEDI-0680 can be administered once every two weeks for up to one year. In embodiments, REGN2810 can be administered once every two weeks. In embodiments, AMP224 can be administered at 10 mg/kg once every two weeks.

Anti-PD-L1 Antibodies: 0.01 mg/kg to 20 mg/kg administered to subject every 1-4 weeks. In embodiments, such administration is for so long as the cancer or infectious disease persists. In embodiments, the administration can be, for example, up to 156 weeks. In embodiments, BMS-936559/MDX-1105 may be administered as, for example, 1, 3, or 10 milligram per kilogram (mg/kg) every 2 weeks, for up to two years; MPDL3280A/RG7446 may be administered as, for example, 1200 mg every three weeks, for up to 1 year or for up to two years or until disease progression; MSB0010718C/avelumab may be administered as, for example, 10 mg/kg once every 2 weeks until disease progression; and MEDI4736 may be administered, for example, every one, two, three, or four weeks for up to one year or up to two years. Effective amounts for some agents are currently being tested in clinical trials and may change accordingly.

Anti-CTLA-4 Antibodies: 0.01 mg/kg to 20 mg/kg every 1-4 weeks. In embodiments, such administration is for so long as the cancer or infectious disease persists. In embodiments, the administration can be, for example, up to 156 weeks. In embodiments, MDX-010/ipilimumab, may be administered at 0.3 mg/kg, 3 mg/kg, 6 mg/kg, or 10 mg/kg every three weeks for four doses or cycles or for up to thirty-two doses, with provision for maintenance treatment every twelve weeks; tremelimumab/CP-675,206 may be administered at 3 mg/kg, 6 mg/kg, 10 mg/kg, or 15 mg/kg every 12 weeks for 4 doses or for up to 8 doses. Effective amounts for some agents are currently being tested in clinical trials and may change accordingly.

Anti-VISTA Antibodies: 0.01 mg/kg to 20 mg/kg administered to subject every 1-4 weeks. In embodiments, such administration is for so long as the cancer or infectious disease persists. In embodiments, the administration can be, for example, up to 156 weeks. Effective amounts for some agents may change according to results from future clinical trials.

Mobilizing Agents: Such agents are given in amounts sufficient to mobilize stem cell from bone marrow into peripheral blood. Such amounts for particular mobilizing agents have been, for example: 1 µg/kg to 20 µg/kg G-CSF per day, preferably, 5 µg/kg or 10 µg/kg G-CSF per day; 1 to 20 mg PEGylated G-CSF, preferably 6 mg or 12 mg PEGylated G-CSF; 1 to 20 µg/kg PEGylated G-CSF per day; 1 to 20 µg/kg lenogratism per day, 1 to 40 µg/m$^2$ C-X-C chemokine receptor type 4 (CXCR-4) per day; 1 to 40 µg/m$^2$ plerixafor per day.

Methods of administration. In some embodiments of the disclosure, immune checkpoint inhibitors are administered intravenously (by intravenous (IV) infusion). Antibodies may also may be administered via other modes of administration known in the art. Such modes of administration include inhalation, ingestion, and topical application. Oral administration is also possible for therapeutics, although this form of administration is more challenging for certain biologics such as antibodies. HSCT is often administered with chemotherapy, which can be administered through various methods. In embodiments of the disclosure, the HSC mobilizing agent is administered orally, subcutaneously, intra-muscularly, intravenously, intraventricularly, intrathecally, intraperitoneally, intra-arterially, intravascularly, or intrapleurally, preferably intravenously.

Adoptive Cell Therapy (ACT or Adoptive Cell Transfer). Adoptive cell therapy is the transfer of cells into a patient for the purpose of transferring immune functionality and other characteristics with the cells. The cells are most commonly immune-derived, for example T cells, and can be autologous or allogeneic. Transfer of autologous cells rather than allogeneic cells minimizes graft versus host disease issues. ACT can be used for treatment of viral infections and/or for reducing the regression of cancer. There is an increased risk for infection and/or malignancy, in a subject receiving immunosuppressive or ablative treatment (e.g., chemo or radiation treatment) in connection, for example, with stem cell transplantation, including HSCT, organ transplantation, and certain types of cancer, wherein immune reconstitution is often slow and incomplete and there is a risk for malignancy. The use of ACT in a subject in the period following immunosuppression is thought to be advantageous to the subject, with the potential for enhancing immunity, including antitumor immunity, and increasing vaccine efficacy in the period following immunosuppression. ACT of tumor-specific T cells has been shown to be effective in treatment of solid tumors in murine and in human systems. In embodiments, ACT is used with HSC infusion or with administration of an HSC mobilizing agent, wherein the addition of HSCs increases the immune response of the subject as shown through an increase of IFNγ secretion.

EXAMPLES

Example 1. Hematopoietic stem cells (HSCs) alter tumor-draining lymph node microenvironment and enhance anti-tumor immunity. HSC transfer leads to increased IFNγ secreting anti-tumor T cells in tumor bearing hosts.

Adoptive cellular therapy (ACT) consisting of intravenous infusion of tumor-specific T cells and intradermal vaccination with dendritic cells was administered to mice bearing intracranial tumors with or without intravenous infusion of HSCs. T cells were derived from mice with yellow fluorescent protein (YFP) under control of an interferon-gamma promoter so that T cells fluoresced when activated. Tumor draining lymph nodes (cervical nodes) were collected from tumor bearing mice after ACT+HSCs, RNA extracted, and examined by PCR array for the expression of a panel of T cell activation markers. The relative expression of genes in the +HSC lymph nodes is shown as a heat map in FIG. 1A. A marked increase in interferon gamma was noted as shown by the red square (D6 which is visible in a color version of FIG. 1A) denoting IFNγ expression. T cells were examined by flow cytometry for YFP (IFNγ) expression (shown on x-axis) in FIG. 1B. Naïve mice showed less than 1% expression of IFNγ, while in vitro expanded tumor specific T cells showed ~3.5% cell reactivity. After ACT without HSCs, the activation state increased to ~64.3% IFNγ secreting T cells. The addition of HSCs markedly enhanced IFNγ secretion with >90% positivity in the presence of HSCs. The enumeration of the IFNγ+ T cells in each group is shown in FIG. 1C.

Adoptive cell therapy. C57BL/6 mice (Jackson Laboratories) were stereotactically implanted with $10^4$ KR158B astrocytoma cells into the right caudate nucleus on Day 0. Mice then received a single dose of non-myeloablative (NMA) 5Gy or myeloablative (MA) 9Gy total body irradiation (TBI) on Day 4. Mice receiving hematopoietic stem cell transfer were given intravenous injection of 5×10$^4$ lin bone marrow derived stem cells within 24 hours of TBI. Intravenous injection of 10$^7$ tumor specific T lymphocytes was administered between 16 and 24 hours after TBI. This was immediately followed by an intradermal vaccination of 2.5×10$^5$ total tumor RNA-pulsed DCs. DC vaccines 2 and 3 were administered at weekly intervals. Isolation of hematopoietic stem cells (HSC)

Hematopoietic stem cell (HSC) isolation. Bone marrow of C57BL/6 mice was harvested from femurs and tibia of mice. Red blood cells were then lysed using ammonium chloride based lysis solution (PharmLyse from BD biosciences) leaving mononuclear cells. Using the Miltenyi Biotec mouse lineage (lin–) depletion kit, these cells were isolated as per manufacturer's instructions. Cells were labelled with Miltenyi biotin labelled antibody cocktail followed by bead conjugated secondary antibody. This solution was then run through a sterile magnetic column to isolate lin– hematopoietic stem cells (HSCs). HSCs were resuspended in sterile phosphate buffered saline and injected intravenously into mice within 2 hours of isolation. Treated mice received 50,000 to 100,000 HSCs in 100 ul final volume.

Generation of tumor specific T cells for adoptive transfer. Total RNA was isolated from KR158B-luc tumor and electroporated into bone marrow derived DCs using BTX Single Waveform Electroporation System (Harvard Apparatus). Naïve mice received intradermal vaccination with total tumor RNA-pulsed DCs, their spleens harvested seven days later, and the splenocytes expanded ex vivo using RNA-pulsed DCs and 100IU IL-2 (R&D Systems) for seven days. T cells were expanded from primed spleens of either wild-type C57BL/6 mice (Jackson Laboratories. Bar Harbor, ME, stock #000664), DsRed transgenic mice on a C57BL/6 background (Jackson laboratories, stock #006051) or GFP transgenic mice on a C57BL/6 background (Jackson Laboratories, stock #004353). Tumor-reactive T cells were adoptively transferred intravenously after 5 to 7 days of in vitro activation.

Generation of RNA-pulsed dendritic cell (DC) vaccines. Dendritic cells (DC) were isolated from the bone marrow of C57BL/6 mice using an altered previously published protocol. Briefly, femurs and tibias of C57BL/6 mice were harvested and bone marrow flushed with RPMI (LifeTechnologies)+10% FBS (LifeTechnologies). Red cells were lysed with 10 mL Pharmlyse (BD Bioscience) and mononuclear cells were re-suspended in CDCM (RPMI-1640, 5% FBS, IM HEPES (LifeTechnologies), 50 µM, 55 mM β-mercaptoethanol (LifeTechnologies), 100 mM Sodium pyruvate (LifeTechnologies), 10 mM Nonessential amino acids (LifeTechnologies), 200 mM L-glutamine (LifeTechnologies), 10 µg GM-CSF (R&D Systems), 10 µg IL-4 (R&D Systems), 5.5 mL Penicillin/Streptomycin (LifeTechnologies)) and plated into tissue culture treated 6-well plates at a density of 10$^6$ cells/mL in a total volume of 3 mL/well. Non-adherent cells were discarded at day 3. At day 7, non-adherent cells were collected and re-plated onto 100 mm tissue treated culture dishes at a density of 10$^6$ cells/mL in a total volume of 5 mL/dish. Twenty four hours later, resulting cells were electroporated with 25 µg of total RNA isolated from KR158B-luc cells (RNeasy, Qiagen). RNA-pulsed DCs were collected the following day and suspended in PBS at a final concentration of 2.5×10$^6$ cells, and 100 µl cell suspension was administered via intradermal injection.

FIG. 1A shows that seven week old female C57BL/6 mice received intracranial injection of 10,000 astrocytoma cells into the right caudate nucleus. On day 4, all mice received 5Gy non-myeloablative total body irradiation. Group 1 received adoptive transfer of tumor specific T cells and DC vaccine only. Group 2 received adoptive transfer of T cells, DC vaccine, and HSC transfer. Lymph nodes were harvested from both groups and RNA isolated. PCR arrays looking at genes associated with T cell activation were run on the RNA from lymph nodes. The figure shows expression in lymph nodes of mice that received HSC transfer relative to those that did not. The results demonstrate a significant increase in IFNγ expression in the group that received HSCs.

Figure 1B:
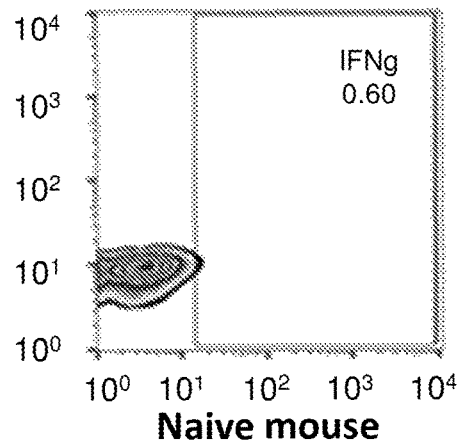
Figure 1B:
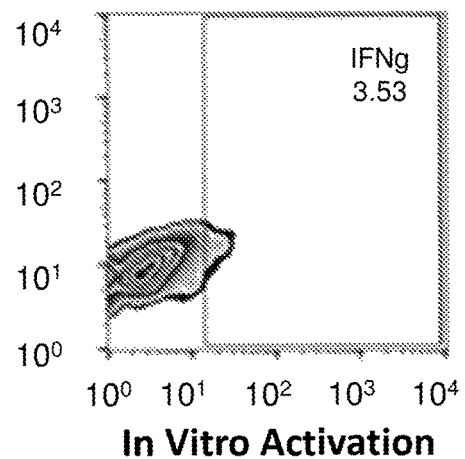
Figure 1B:
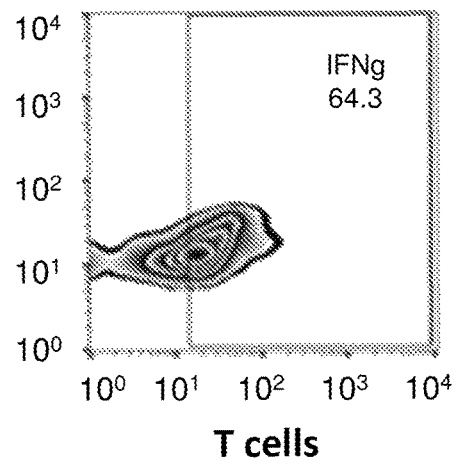
Figure 1B:
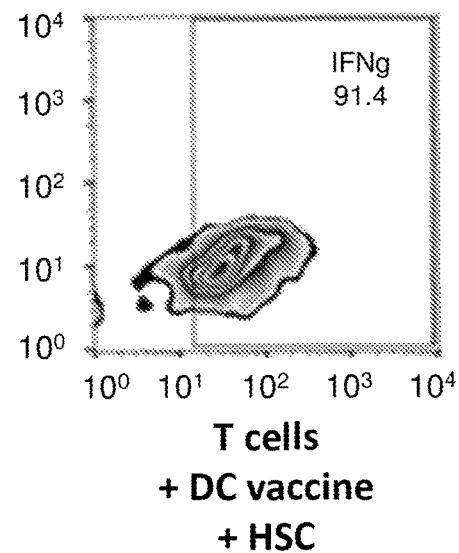
Figure 1C:
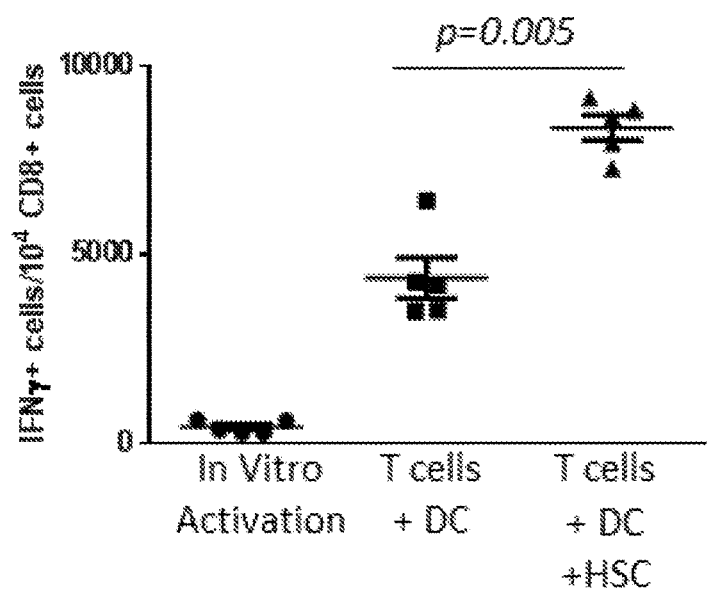

FIGS. 1B and 1C show results of experiments, wherein the same experiment as in FIG. 1A was conducted, but using T cells generated from YETI mice that express yellow fluorescent protein (YFP) on an IFNγ promoter. Thus cells with anti-tumor function (IFNγ secretion) are easily detectable using flow cytometry. Spleens of these mice were analyzed for YFP as were newly generated tumor specific T cells. Little to no YFP was found on splenocytes, and only 3-7% of in vitro expanded T cells expressed YFP. These cells were then used for adoptive transfer into a tumor bearing mouse in the context of 5Gy non-myeloablative host conditioning. Group 1 received T cells and DC vaccine only, while Group 2 received HSCs, T cells, and DC vaccine. The tumor draining lymph nodes were excised and analyzed for YFP expression. Mice in group 2 (T cells, DC vaccine, and HSC transfer) revealed significant increases in T cell activation. HSC transfer leads to increased IFNγ secreting anti-tumor T cells in tumor bearing hosts. FIG. 2 shows that a combination of HSCs with immune checkpoint inhibitors potentiate increased IFNγ secretion by tumor infiltrating host cells.

Example 2. Hematopoietic stem cells (HSCs) alter tumor microenvironment and restore responsiveness to immune checkpoint blockade. Combination of HSCs with immune checkpoint inhibitors potentiate increased IFNγ secretion by tumor infiltrating host cells.

Figure 2A:
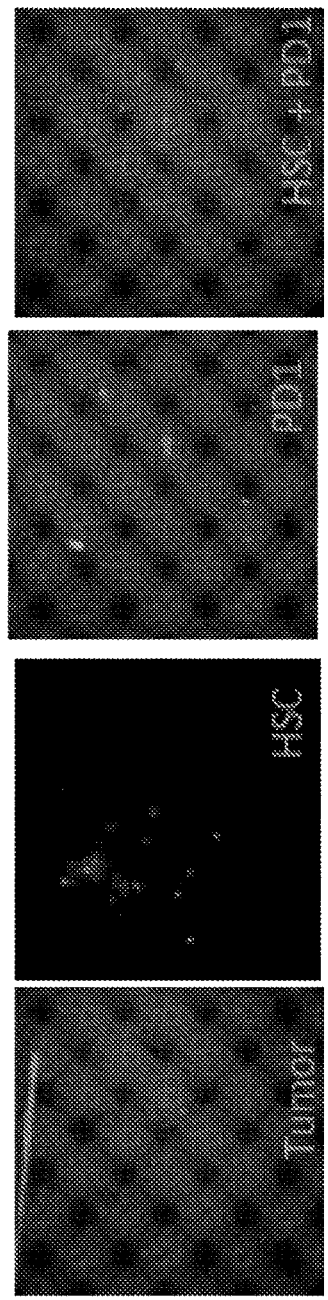
FIG. 2A shows the expected results when YETI mice (IFNγ reporter mice whose cells fluoresce when producing IFNγ) are implanted with 10,000 astrocytoma cells intracranially. On day 3, mice receive either intravenous injection of HSCs, intraperitoneal injection of anti-PD-1 antibody, or both. Using YETI host mice, it was easy to determine whether T cell activation was occurring. Thirty days later, tumors were excised and sectioned into 500 mm slices using a tissue slicer.
Figure 2B:
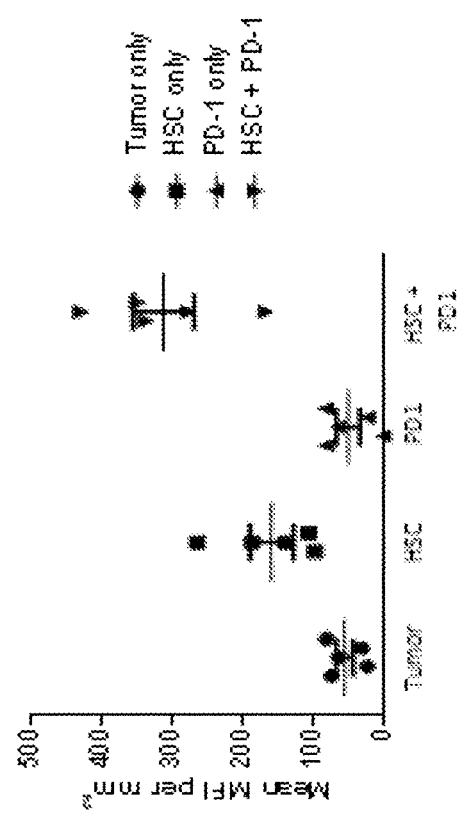
FIG. 2B shows that fluorescence was detected using the Olympus IX70 inverted fluorescent microscope, and quantified by determining MFI per slice. The group that received anti-PD-1 antibody and HSCs had significantly higher YFP expression than the other groups.
Figure 3:
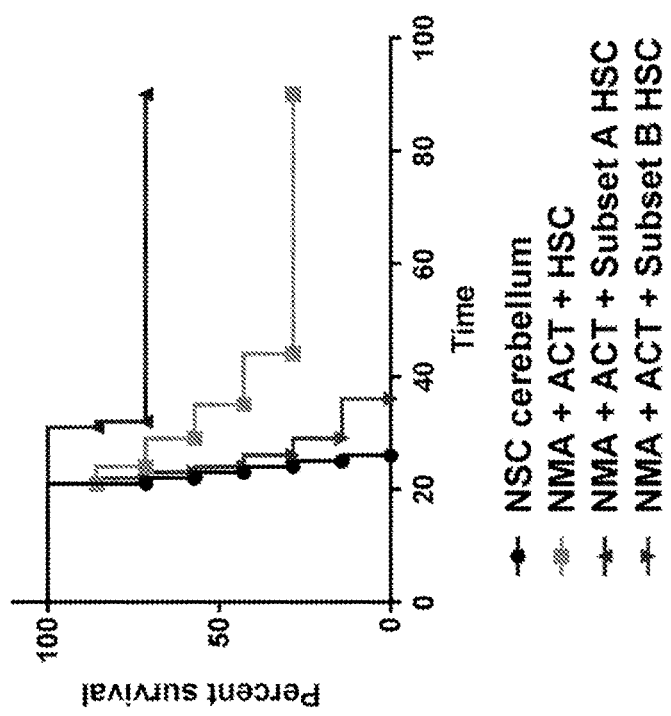
FIG. 3 shows that specialized HSC subsets mediate enhanced anti-tumor immunity against malignant glioma.
Figure 4:
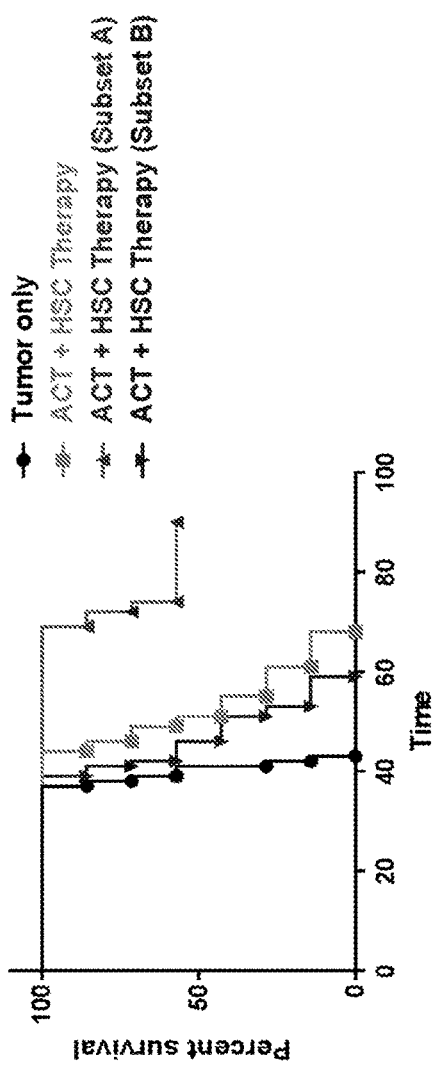
FIG. 4 shows that specialized HSC subsets mediate enhanced anti-tumor immunity against medulloblastoma.

The observation that HSCs alter the microenvironment of lymph nodes and permit the increased activation of T cells as shown by IFNγ production, prompted us to examine the impact of HSC transfer on the tumor microenvironment and activation state of immune cells within intracranial tumors. The tumor microenvironment is known to be profoundly immunosuppressive leading to the shutdown of anti-tumor immune cells and failure of immunologic tumor rejection. We showed that HSC transfer alone leads to an increase in intratumoral IFNγ-secreted cells as shown in FIG. 2A & FIG. 2B. This increase was greater than that induced by anti-PD-1 monoclonal antibody PD1 blockade. However, HSC transfer alone or anti-PD-1 monoclonal antibody treatment alone were unable to prolong survival in a meaningful way in tumor bearing animals (FIG. 2C). However, the combination of HSCs+anti-PD-1 antibody showed profound synergy in intratumoral immune activation as shown by IFNγ secretion (FIG. 2B) and led to marked improved survival and long term cures in >40% of treated animals (FIG. 2C). These results demonstrate the novel role of HSCs in altering the tumor microenvironment and potentiating anti-tumor immunity in animals treated with anti-PD-1 antibody. These effects allow for a refractory tumor to become sensitive to anti-PD-1 antibody treatment. Results of anti-PD-1 monoclonal antibody treatment to induce immune checkpoint blockade in combination with administering HSCs suggest to the inventors herein that antagonists targeting other immune checkpoint inhibitors, e.g., CTLA-4, may be useful in combination therapy with HSCs. Synergistic effects of a combination of anti-PD-1 monoclonal antibody treatment to induce immune checkpoint blockade in combination with administering HSCs, disclosed herein suggest that antagonists targeting other immune checkpoints, e.g., PD-L1,CTLA-4, and/or VISTA will be useful in combination therapy with HSCs.

Combining HSC therapy and treatment with a CTLA-4 antagonist yielded inconclusive results (data not shown). However, results obtained with combinatorial therapy of HSC transfer and PD-1 or VISTA antagonism, indicate that other immune checkpoint antagonists may yield a synergistic effect when combined with HSC transfer. Treatment with more than one agent that antagonizes an immune checkpoint(s) in combination with HSC transfer may result in synergistic effects. In some embodiments, one or more agents that antagonize one or more immune checkpoint molecules, e.g., PD-1, PD-L1, CTLA-4, and/or VISTA are administered in combination therapy with HSCT therapy. In some embodiments, synergistic effects may occur by administering one or more agents that antagonize one or more immune checkpoint molecules, e.g., PD-1, PD-L1, CTLA-4, and/or VISTA in combination with HSC transfer and/or HSC mobilization treatment.

Example 3. Synergistic effects of HSC transfer and immune checkpoint inhibitor combination therapy is further potentiated with radiation therapy.

Immunocompetent C57BL'6 mice received intracranial tumors, then divided into seven groups: Group 1: tumor only; Group 2: lineage negative hematopoietic stem cells (HSC); Group 3: anti-PD1 antibody (αPD1); Group 4: HSC+αPD1; Group 5: total body irradiation with 500 rads+HSC; Group 6: total body irradiation with 500 rads+αPD1; and Group 7: total body irradiation with 500 rads+HSC+αPD1. For total body irradiation, x-ray irradiation for a single dose of 500 rads was administered four days post-tumor implantation. For intravenous HSC administration, a single dose of $10^5$ cells in sterile saline at a final volume of 100 ul was administered five days post-tumor implantation. For intraperitoneal αPD1, 10 mg/kg was administered every 5 days for a total of 4 doses, with starting dose at five days post-tumor implantation.

Figure 5:
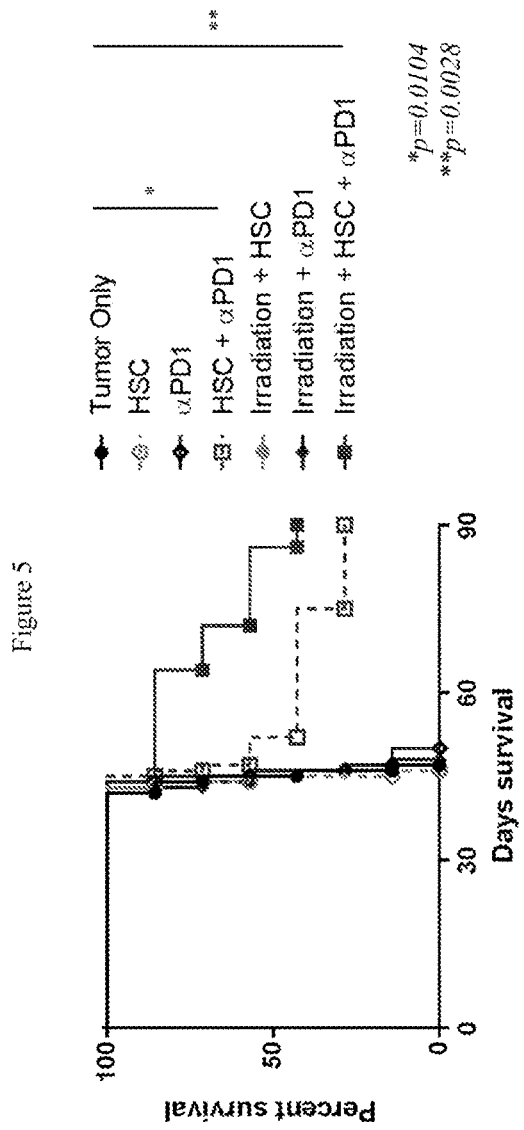
FIG. 5 shows survival of immunocompetent C57BL/6 mice that received intracranial tumors that were untreated or treated with HSCs, anti-PD1 antibody, HSCs and anti-PD1 antibody, irradiation and HSCs, irradiation and anti-PD1 antibody, or irradiation, HSCs, and anti-PD1 antibody.

FIG. 5 shows results of the experiment: median survival was significantly extended from 45 days in the tumor only control group, to 52 days in animals that received HSC+αPD1 (p=0.0104); median survival was also significantly extended in the group that received 500 rad total body irradiation+HSC+αPD1 relative to tumor only controls (p=0.0028). Importantly, the group that received HSC+αPD1 showed significant benefit in median survival relative to αPD1 alone group (p=$0.0^{237}$). With addition of irradiation, tumor bearing mice that received irradiation+HSC+αPD (86 days) had significantly extended median survival over the group that received irradiation+αPD1 (45 days) (p=0.0018). There is no statistically significant difference in survival between HSC+αPD1 group and irradiation+HSC+αPD1 group (p=0.04393).

Example 4. Combination of treatment with HSCs and immune checkpoint blockade using anti-VISTA antibody results in increased survival of mice with anti-VISTA resistant tumors.

Immunocompetent C57BL/6 mice received intracranial tumors and were then divided into four groups: Group 1: tumor only; Group 2: lineage negative hematopoietic stem cells (HSC); Group 3: antibody against V-domain Ig suppressor of T-cell activation (VISTA)(αVISTA); and Group 4: HSC+αVISTA. For intravenous HSC administration, a single dose of $10^5$ cells in sterile saline at a final volume of 100 ul was administered five days post-tumor implantation. For intraperitoneal αVISTA, a 300 ug dose was administered every 3 days for a total of four doses.

Figure 6:
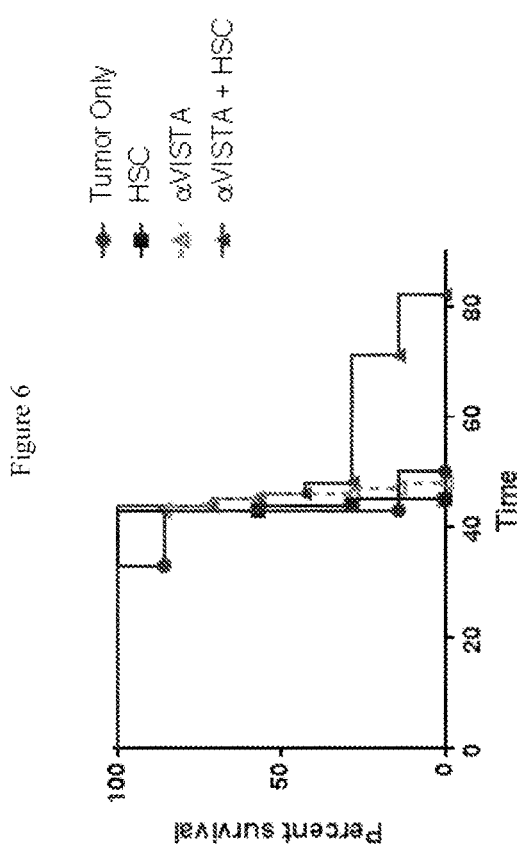
FIG. 6 shows survival of immunocompetent C57BL/6 mice that received intracranial tumors that were untreated or treated with HSCs, anti-VISTA antibody, or HSCs and anti-PD1 antibody.

FIG. 6 shows results of the experiment: median survival was significantly extended from 43 days in the tumor only control group to 46 days in animals that received HSC+αVISTA (p=0.0332). These results indicate that other immune checkpoint inhibitors can be targeted in combination with HSC therapy in a subject to treat disease, e.g., cancer and/or infectious disease, and increase survival.

Example 5. CCR2 positive (CCR2pos or CCR2+) HSCs enhance the effect of HSC therapy in combination with αPD1 treatment.

Immunocompetent C57BL/6 mice received intracranial gliomas and were divided into eight groups: Group 1: tumor only; Group 2: lineage negative hematopoietic stem cells (HSC); Group 3: HSCs that do not express CCR2 (CCR2neg HSC); Group 4: HSCs that express CCR2 (CCR2pos HSC); Group 5: αPD1; Group 6: PD1+HSC; Group 7: αPD1+CCR2neg HSC; and Group 8: αPD1+CCR2pos HSC. Negative expression selection of lineage commitment markers (lineage negative (Lin–)) and positive selection of CCR2 (CCR2pos) on HSCs was performed alone and in combination with αPD1 treatment. For CCR2+HSC selection, bone marrow derived cells were first isolated using a magnetic lineage depletion kit (Miltenyi Biotec). Resulting HSCs were then stained using biotinylated anti-CCR2 antibody (Miltenyi Biotec). An anti-biotin antibody conjugated to magnetic bead was then added, and the cell suspension was then run through a magnetic column. Resulting cell fractions were CCR2neg HSCs and CCR2pos HSCs.

Figure 7:
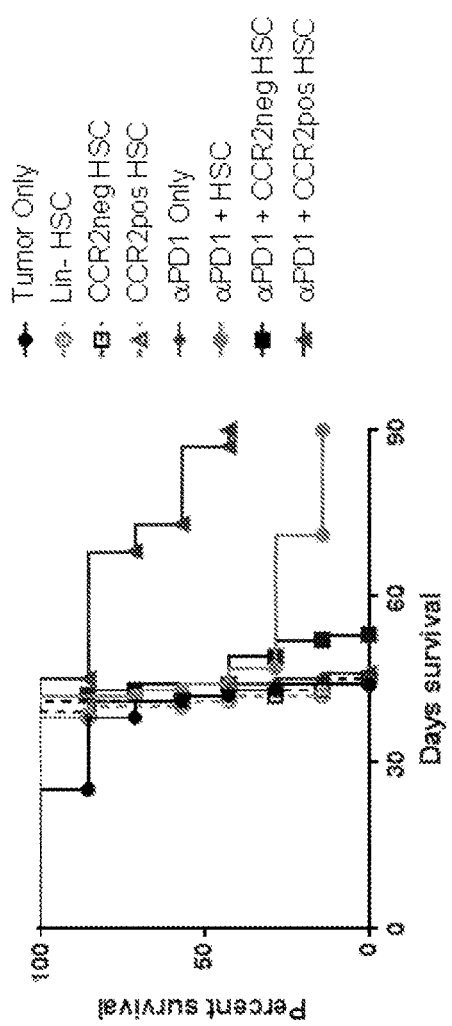
FIG. 7 shows survival of immunocompetent C57Bl6 mice that received intracranial tumors that were untreated or treated with lineage negative hematopoietic stem cells (Lin– HSC), HSCs that do not express CCR2 (CCR2neg HSC), HSCs that express CCR2 (CCR2pos HSC), αPD1, αPD1+ HSC, αPD1+CCR2neg HSC, or αPD1+CCR2pos HSC.

Results are shown in FIG. 7: the median survival of the group the received αPD1+CCR2pos HSCs significantly increased over the group that received HSC+αPD1 (p=0.0323). It was an unexpected finding and previously undescribed that the CCR2pos HSCs enhance immunity. The use of this specialized subset of CCR2+HSCs may be more beneficial in combination with immune checkpoint blockade.

Example 6. HSC transfer in combination with PD-1 blockade enhances lymphocyte function and maintains T cell activation in tumor microenvironment-IFN gamma production is maintained in the tumor microenvironment.

Immunocompetent mice received intracranial tumors and were divided into four groups: Group 1: tumor only; Group 2: tumor+HSC; Group 3: tumor+αPD-1; and Group 4: tumor+HSC+αPD-1. Mice used as tumor bearing hosts express yellow fluorescent protein (YFP) when secreting interferon gamma (IFNγ). For intravenous HSC administration, a single dose of 105 cells in sterile saline at a final volume of 100 ul was administered five days post-tumor implantation. For intraperitoneal αPD1, a 10 mg/kg dose was administered every 5 days for a total of 4 doses, with starting dose at five days post-tumor implantation.

Figure 8A:
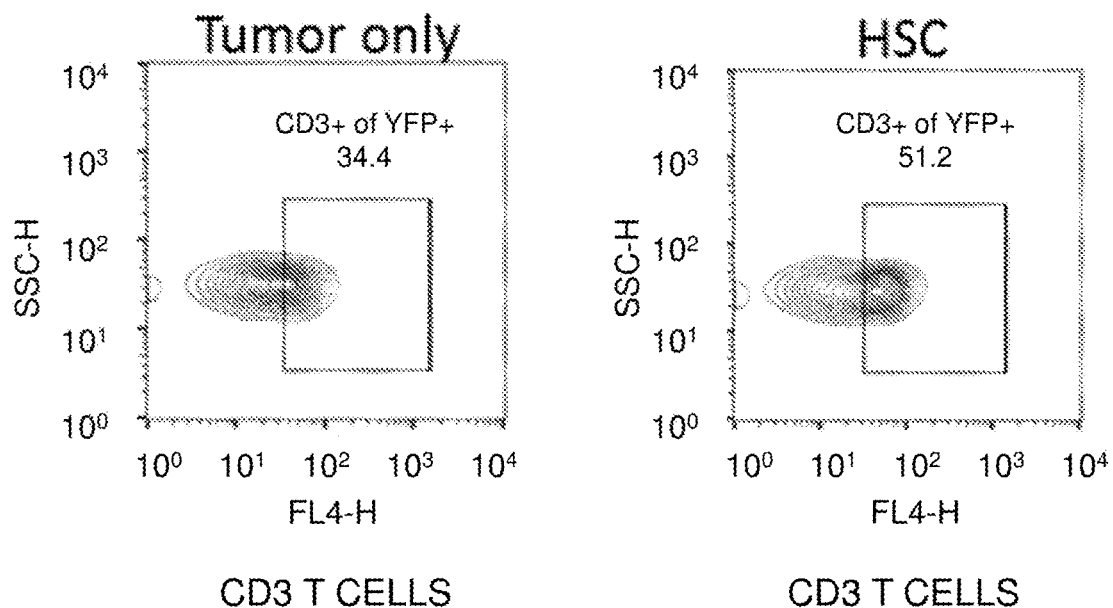
Figure 8A:
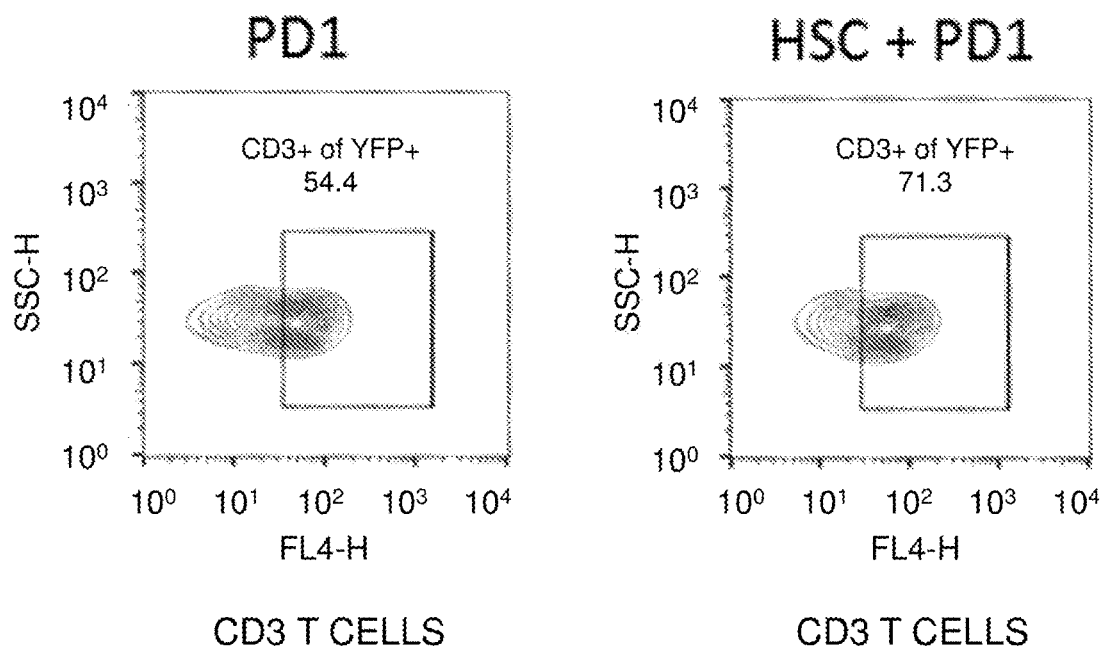
Figure 8A:
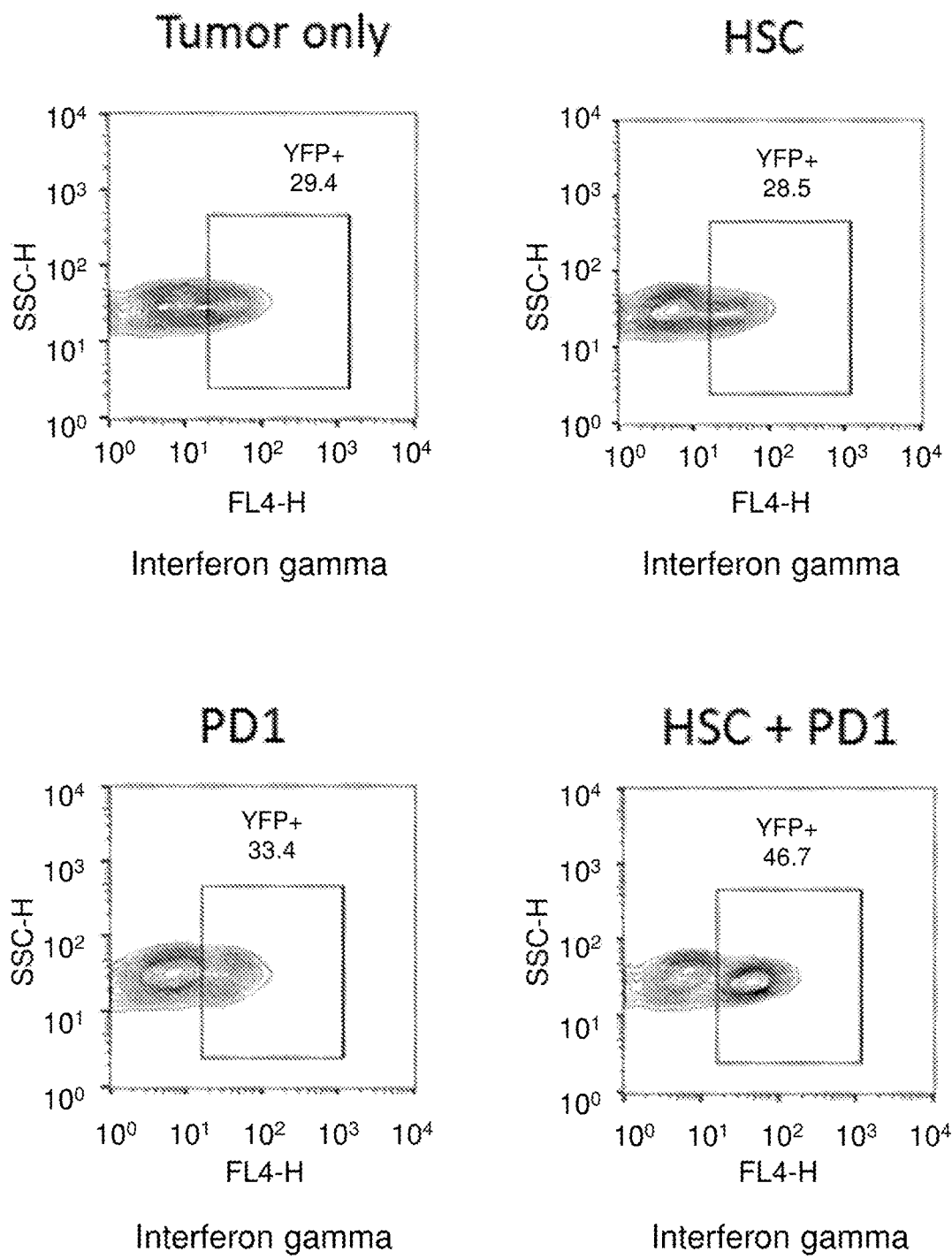

Results are shown in FIGS. 8A and 8B: quantification (FIG. 8B) by flow cytometric analysis (FIG. 8A) of YFP/IFNγ+CD3+ lymphocytes within the tumor microenvironment in untreated mice and mice treated with either HSC, anti-PD1, or both HSC+anti-PD1. The results show that IFNγ secretion by CD3+ T cells in groups treated with combinatorial therapy is significantly increased (p-value=0.001). This demonstrates that HSC+anti-PD1 treatment leads to increased frequency of tumor infiltrating lymphocytes with anti-tumor reactivity.

Example 7. HSCs enhance lymphocyte function in tumor microenvironment with PD-1 blockade.

Immunocompetent C57BL/6 mice received intracranial tumors and were divided into four groups: Group 1: tumor only; Group 2: tumor+HSC; Group 3: tumor+PD-1; and Group 4: tumor+HSC+αPD-1. For intravenous HSC administration, a single dose of 105 cells in sterile saline at a final volume of 100 ul was administered 14 days post-tumor implantation. For intraperitoneal αPD1, a 10 mg/kg dose was administered every 5 days for a total of 4 doses, starting dose at 14 days post-tumor implantation. 35 days post tumor implantation, tumors were harvested and RNA was isolated using commercially available kit (Qiagen). RNA from samples were analyzed using a T-Cell & B-cell Activation RT2 PCR array (SA Biosciences) following manufacturer's instructions.

Figure 9:
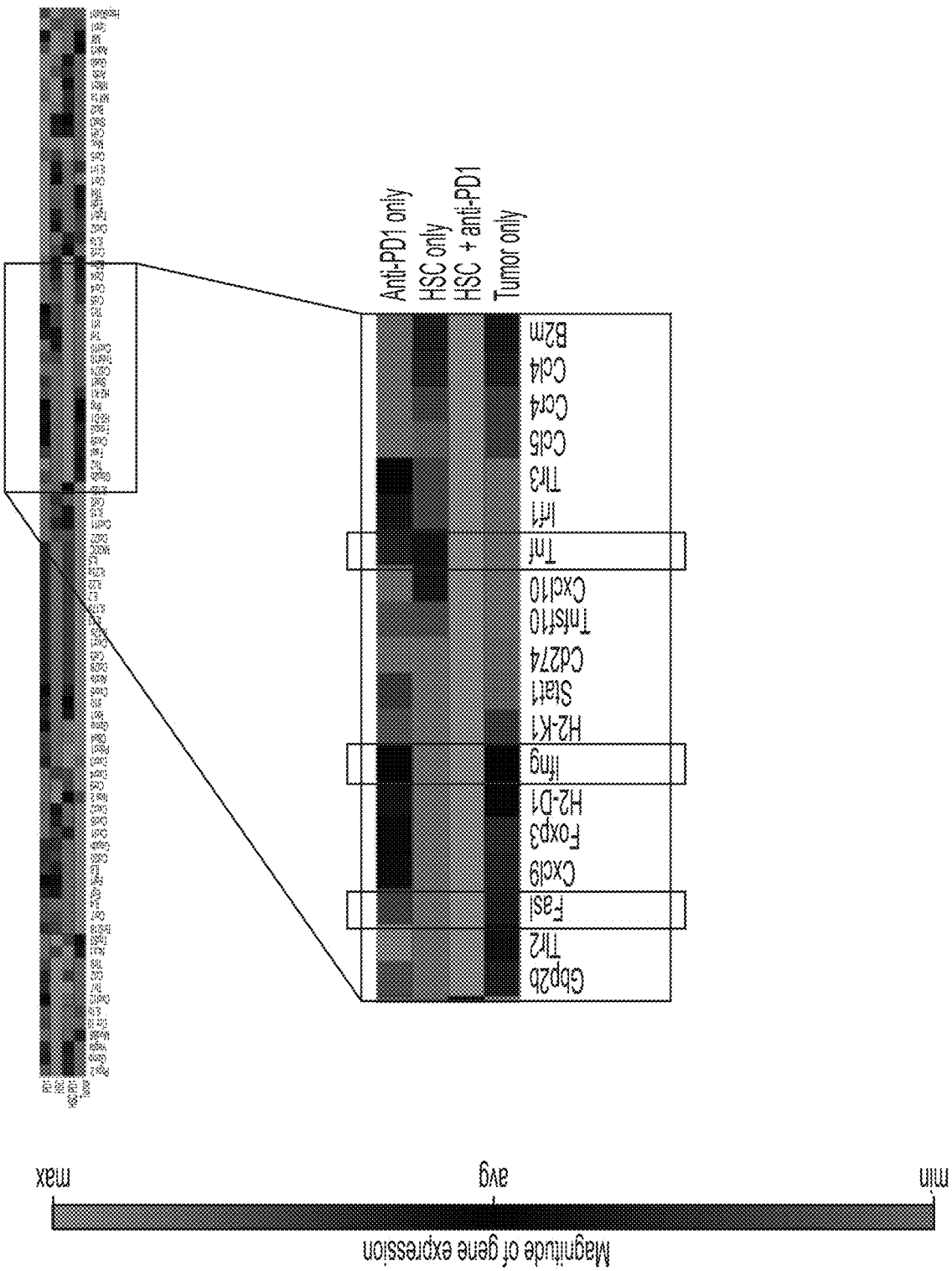
FIG. 9 shows expression of 92 genes involved in T cell activation/inflammatory pathway, in immunocompetent C57BL/6 mice that received intracranial tumors that were untreated or treated with HSC, αPD-1, or HSC and αPD-1.

Genetic analysis of tumors from mice treated with HSC only, anti-PD1 only, or both HSCs+anti-PD1 was performed. Results are shown in FIG. 9: the magnified portion of the gene expression heat map shows that a number of genes involved in T cell activation/inflammatory pathway, e.g., Fas1, IFNγ, and TNF, are highly upregulated in Group 4 (Tumor+HSC+αPD-1 treatment). The results demonstrate that combinatorial HSC+anti-PD treatment increases markers associated with activated cytotoxic T cells, including IFNγ. We have also found an upregulation of chemokines which are known mediators of T cell migration.

The invention claimed is:

1. A method for treating a cancer comprising administering to a subject having the cancer one or more immune checkpoint inhibitors, and administering to the subject hematopoietic stem cells, in amounts effective to treat the cancer, wherein the one or more immune checkpoint inhibitors are each an antagonist of cytotoxic T-lymphocyte-associated antigen 4 (CTLA-4), and/or B7 family inhibitory ligand B7-H3, and wherein the source of hematopoietic stem cells is autologous or wherein the source of hematopoietic stem cells is allogenic and the donor cells are HLA-matched to the recipient.

2. The method of claim 1, wherein the cancer is resistant to monotherapy treatment with the one or more immune checkpoint inhibitors.

3. The method of claim 1, wherein the CTLA-4 antagonist is an agent that binds to and antagonizes CTLA-4.

4. The method of claim 3, wherein the agent that binds to and antagonizes CTLA-4 is a peptide that binds CTLA-4 or a humanized antibody that selectively binds CTLA-4.

5. The method of claim 1, wherein the B7-H3 antagonist is an agent that binds to and antagonizes B7-H3.

6. The method of claim 5, wherein the agent that binds to and antagonizes B7-H3 is a peptide that binds B7-H3 or a humanized antibody that selectively binds B7-H3.

7. The method of claim 1, wherein the immune checkpoint inhibitor is administered on the same day or on a different day than the hematopoietic stem cell transplantation.

8. The method of claim 1, wherein the immune checkpoint inhibitor is administered within 3 months of the hematopoietic stem cells.

9. The method of claim 1, wherein the immune checkpoint inhibitor is administered within 1 month of the hematopoietic stem cells.

10. The method of claim 1, wherein the immune checkpoint inhibitor is administered within 1 week of the hematopoietic stem cells.

11. The method of claim 1, wherein the immune checkpoint inhibitor is administered within 1 day of the hematopoietic stem cells.

12. The method of claim 1, further comprising administering to the subject a hematopoietic stem cell mobilizing agent.

13. The method of claim 1, wherein the cancer is melanoma, squamous cell carcinoma, basal cell carcinoma, breast cancer, head and neck carcinoma, thyroid carcinoma, soft tissue sarcoma, bone sarcoma, testicular cancer, prostatic cancer, ovarian cancer, bladder cancer, skin cancer, brain cancer, glioblastoma, medulloblastoma, ependymoma, angiosarcoma, hemangiosarcoma, mast cell tumor, primary hepatic cancer, small cell lung cancer, non-small-cell lung cancer, pancreatic cancer, gastrointestinal cancer, renal cell carcinoma, hematopoietic neoplasia, lymphoma, mesothelioma, glioblastoma, low-grade glioma, high-grade glioma, pediatric brain cancer, medulloblastoma, or a metastatic cancer thereof.

14. The method of claim 1, wherein the source of hematopoietic stem cells is bone marrow, bone marrow lineage depleted cells (lin-), cKit+ purified lineage negative bone marrow derived cells, Sca+ purified lineage negative bone marrow derived cells, cKit+Sca+ purified bone marrow derived cells, mobilized from host bone marrow using GM-CSF, G-CSF, mobilized from host bone marrow using AMD3100, Plerixafor, or the molecule 1,1'-[1, 4-phenylenebis(methylene)]bis [1,4,8,11-tetraazacyclotetradecane], umbilical cord blood or cord-blood derived stem cells, human leukocyte antigen (HLA)-matched blood, mesenchymal stem cells derived from blood or marrow, hematopoietic stem cells differentiated from induced pluripotent stem cells, mobilized peripheral blood, peripheral blood, hematopoietic stem cell subsets including lin- cells purified with CCR2+ marker, lineage negative purified peripheral blood, or CD34+ enriched peripheral blood.

15. The method of claim 1, wherein an effect of the treatment on the cancer is assessed by measuring interferon gamma (IFNγ) secretion by T cells obtained from within a tumor microenvironment or tumor draining lymph nodes of the subject, wherein a synergistic effect is noted if the presence of IFNy is increased with combination therapy.

16. The method of claim 1, wherein at least 5, 10, 15, 20, 25, 30, 35, 40, 45, or 50 percent of the hematopoietic stem cells are CCR2 positive (CCR2+), CD34 positive (CD34+), and/or lineage negative (lin-) cells.

17. The method of claim 1, wherein the hematopoietic stem cells for administration to the subject are enriched ex-vivo for CCR2 positive (CCR2+) cells, for CD34 positive (CD34+) cells and/or for lineage negative (lin-) cells prior to administration to the subject.

18. The method of claim 1, wherein the hematopoietic stem cells are processed ex-vivo to deplete CCR2 negative (CCR2-) cells before administration to the subject.

19. A method for treating a cancer comprising administering to a subject having the cancer one or more immune checkpoint inhibitors, and administering a hematopoietic stem cell mobilizing agent, in amounts effective to treat the cancer, wherein the one or more immune checkpoint inhibitors are each an antagonist of cytotoxic T-lymphocyte-associated antigen 4 (CTLA-4), and/or B7 family inhibitory ligand B7-H3.

20. A method for treating a cancer in a subject receiving immune checkpoint inhibitor therapy for the cancer, comprising administering to the subject hematopoietic stem cells in an amount which, in combination with the immune checkpoint inhibitor therapy, is effective to treat the cancer, wherein the one or more immune checkpoint inhibitors are each an antagonist of cytotoxic T-lymphocyte-associated antigen 4 (CTLA-4), and/or B7 family inhibitory ligand B7-H3.

21. A method for treating a cancer in a subject receiving hematopoietic stem cell transplantation therapy for the cancer, comprising administering to the subject one or more immune checkpoint inhibitors in an amount which, in combination with the hematopoietic stem cell transplantation therapy, is effective to treat the cancer, wherein the one or more immune checkpoint inhibitors are each an antagonist of cytotoxic T-lymphocyte-associated antigen 4 (CTLA-4), and/or B7 family inhibitory ligand B7-H3.

22. A method of treating a subject comprising, administering a stem cell mobilizing agent to the subject, harvesting hematopoietic stem cells from the subject, enriching the harvested stem cells for CCR2 positive (CCR2+) , CD34 positive (CD34+), or lineage negative (lin-) cells, administering to the subject the enriched harvested stem cells, and administering to the subject an immune checkpoint inhibitor, wherein the one or more immune checkpoint inhibitors are each an antagonist of cytotoxic T-lymphocyte-associated antigen 4 (CTLA-4), and/or B7 family inhibitory ligand B7-H3.

* * * * *